(12) United States Patent
Baxter-Jones

(10) Patent No.: US 6,450,977 B1
(45) Date of Patent: Sep. 17, 2002

(54) DEVICES AND METHODS FOR CERVIX MEASUREMENT

(75) Inventor: Rosalyn Baxter-Jones, San Diego, CA (US)

(73) Assignee: Cervilenz, Irvine, CA (US)

( * ) Notice: Subject to any disclaimer, the term of this patent is extended or adjusted under 35 U.S.C. 154(b) by 37 days.

(21) Appl. No.: 09/721,513

(22) Filed: Nov. 17, 2000

Related U.S. Application Data

(63) Continuation-in-part of application No. 09/546,099, filed on Apr. 10, 2000.

(51) Int. Cl.$^7$ .............................................. A61B 5/103
(52) U.S. Cl. ..................................................... 600/591
(58) Field of Search ................................ 600/591, 587, 600/300; 33/836; 128/841; 264/222, DIG. 30

(56) References Cited

U.S. PATENT DOCUMENTS

| | | | |
|---|---|---|---|
| 3,630,190 A | 12/1971 | Baker ............................ | 128/2 |
| 3,706,307 A | 12/1972 | Hasson ......................... | 600/591 |
| 4,016,867 A | 4/1977 | King et al. ..................... | 128/2 |
| 4,121,572 A | * 10/1978 | Krzeminksi .................. | 600/591 |
| 4,224,951 A | 9/1980 | Hasson ......................... | 128/778 |
| 4,489,732 A | 12/1984 | Hasson ......................... | 128/778 |
| 4,685,474 A | 8/1987 | Kurz et al. ................... | 128/778 |
| 5,186,180 A | * 2/1993 | Bellas .......................... | 600/591 |
| 5,658,295 A | 8/1997 | Krementsov ................. | 606/119 |
| 5,980,804 A | * 11/1999 | Koch ........................... | 128/841 |

OTHER PUBLICATIONS

Phillip G. Stubblefield, M.D., "Preterm Birth: Causes, Prevention, and Management, Cervical Incompetence", Chapter 6, pp. 98–111 (1984).

I. Brook et al., Ultrasonography in the Diagnosis of Cervical Incompetence in Pregnancy–A New Diagnostic Approach, British Journal of Obstetrics and Gynecology, Jun. 1981, vol. 88, pp. 640–643.

Rush et al., "Contribution of preterm delivery to perinatal mortality." British Medical Journal 2:965–968 (1976).

Villar et al., "Pre–term delivery syndrome: the unmet need." Res. Clin. Forums 16(3):9–33 (1994).

Anderson et al., "Prediction of risk for preterm delivery by ultrasonographic measurement of cervical length." Am. J. Obstet. Gynecol. 163(3):859–867 (1990).

Iams et al., "The length of the cervix and the risk of spontaneous premature delivery." N. Eng. J. Med. 334(9):567–72 (1996).

Health et al., "Cervical length at 23 weeks of gestation: prediction of spontaneous preterm delivery." Ultrasound Obstet. Gynecol. 12:312–317 (1998).

Sonek et al., "Preterm Birth, Causes, Prevention and Management." Second Edition, chapter 5, McGraw–Hill, Inc. pp. 137–160 (1993).

Brook et al., J. Obstet. Gynecol 88:640 (1981).

Michaels et al. "Ultrasound differentiation of the competent from the incompetent cervix: Prevention of preterm delivery." Am. J. Obstet. Gynecol. 154(3):537–546 (1986).

(List continued on next page.)

Primary Examiner—Kevin Shaver
Assistant Examiner—Brian Szmal
(74) Attorney, Agent, or Firm—Lyon & Lyon LLP

(57) ABSTRACT

The present invention provides devices having an elongated member, a slidable indicator slidably engaged with the member and preferably a measuring scale to determine dimensions of female reproductive organs. Preferably, the device is adapted to determine the length of the cervix in the fornix vaginae, which is used in the disclosed methods to predict the risk of preterm labor, the risk of miscarriage, ease or difficulty of inducing labor, and fertility of an individual. Additional embodiments of the device determine dimensions of the fornix vaginae and dilation of the cervix uteri.

27 Claims, 10 Drawing Sheets

OTHER PUBLICATIONS

Sarti et al. "Ultrasonic Visualization of a Dilated Cervix During Pregnancy." Radiology 130:417–420 (1979).

Vaalamo and Kivikoski, "The incompetent Cervix During Pregnancy Diagnosed by Ultrasound." Acta Obstet. Gynecol. Scand 62:19–21 (1983).

Anderson et al., "Relationship between length of gestation and cervical dilatation, uterine contractility, and other factors during pregnancy." Am. J. Obst. & Gynec. 105(8):1207–1214 (1969).

Phillip G. Stubblefield, "Preterm Birth, Causes, Prevention, and Management." Second Edition, Chapter 1, McGraw–Hill, Inc. (1993).

Wood et al., "The prediction of premature labor by observation of the cervix and external tocography." Am. J. Obst. & Gynec. 91(3):396–402 (1965).

Nzeh and Adetoro, "Sonographic assessment of the imcompetent cervix in pregnancy." Int. J. Gynecol. Obstet. 37:179–184 (1992).

Norwitz et al., "The Control of Labor." New Eng. J. of Med. 341(9)660–666 (1999).

* cited by examiner

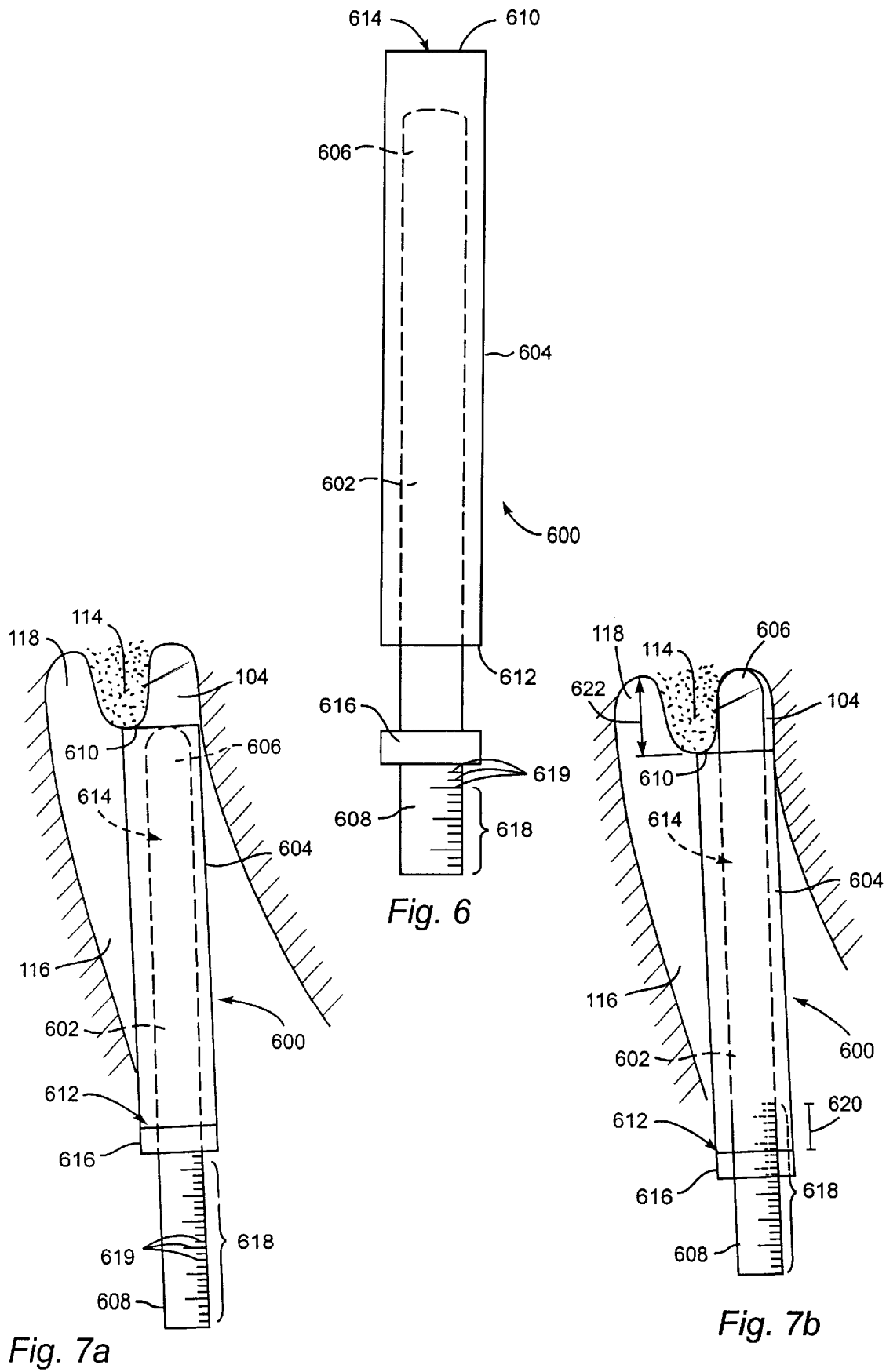

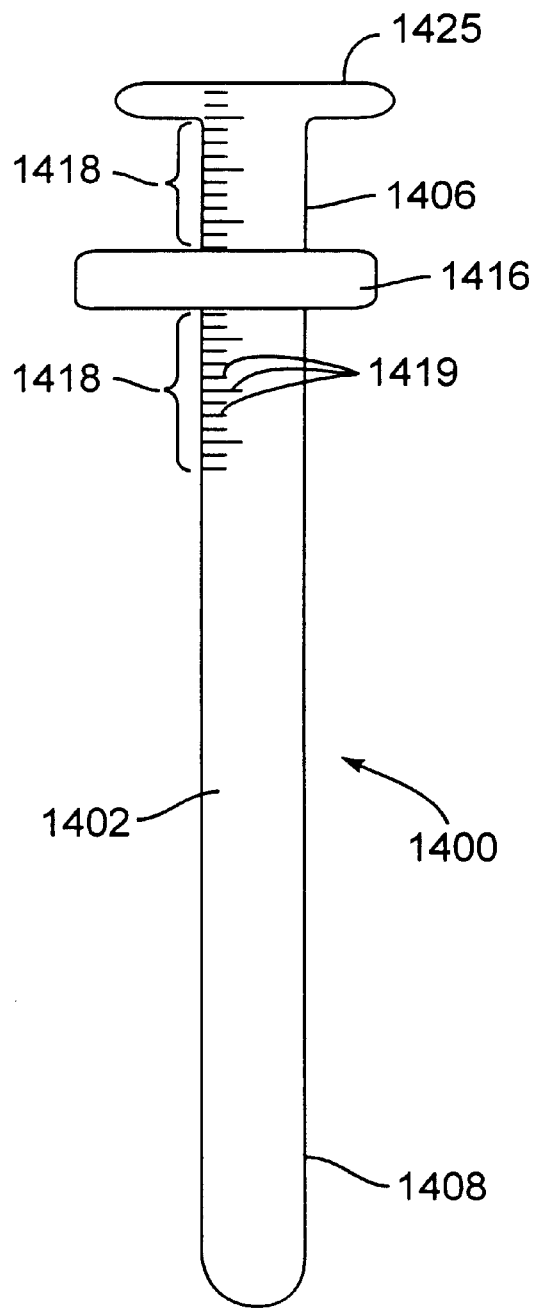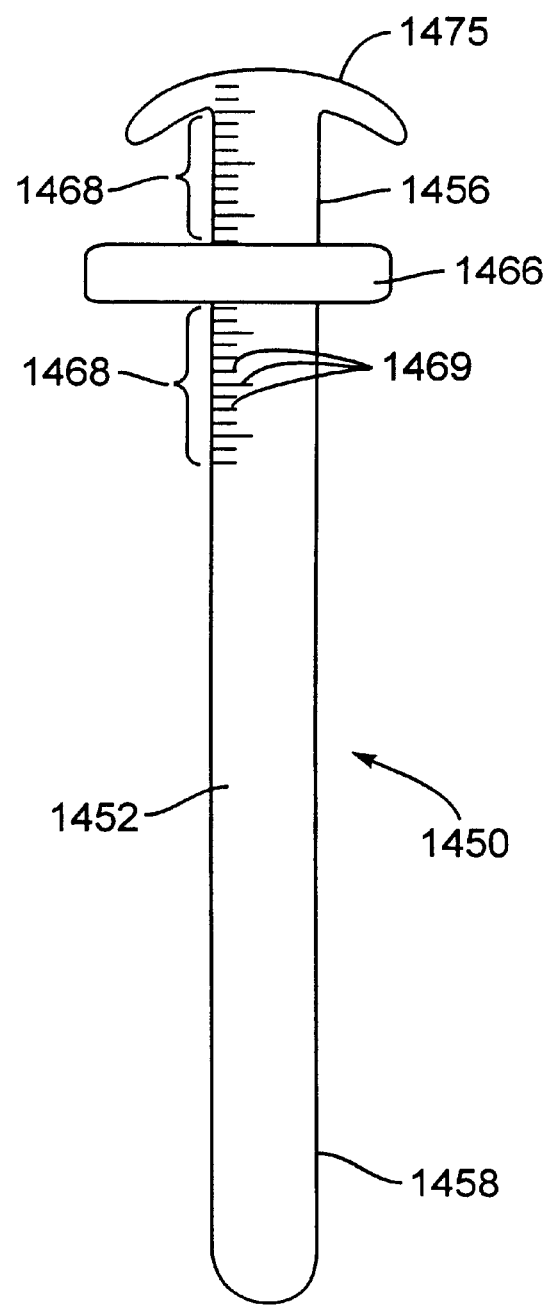
Fig. 14a
Fig. 14b

DEVICES AND METHODS FOR CERVIX MEASUREMENT

CROSS-REFERENCE TO RELATED APPLICATIONS

This application is a continuation-in-part of application Ser. No. 09/546,099, filed Apr. 10, 2000, for Devices and Methods for Cervix Measurement, the disclosure of which is incorporated by reference.

FIELD OF THE INVENTION

The present invention relates to medical devices and methods of using such devices. More particularly, the invention relates to instruments and methods to measure the length of the cervix in the fornix vaginae and the dilation of the cervix uteri.

BACKGROUND

Preterm labor, or labor before 37 weeks gestation, has been reported in 7 to 10 percent of all births but accounts for more than 85 percent of all perinatal complications and death. Rush et al., *BMJ* 2:965–8 (1976) and Villar et al., *Res. Clin. Forums* 16:9–33 (1994), which are both incorporated herein by reference. An inverse relationship between cervical length in the fornix vaginae and the risk of preterm labor has also been observed. Anderson et al., *Am. J. Obstet. Gynecol.* 163:859 (1990); Iams et al., *N. Eng. J. Med.* 334:567–72 (1996) and Heath et al., and *Ultrasound Obstet. Gynecol.* 12:312–7 (1998), which all are incorporated herein by reference. Accordingly, many physicians find it useful to examine the cervix in the fornix vaginae as part of normal prenatal care in order to assess risk of preterm labor.

It has long been known that the cervix normally undergoes a series of physical and biochemical changes during the course of pregnancy, which enhance the ease and safety of the birthing process for the mother and baby. For example, in the early stages of labor the tissues of the cervical canal soften and become more pliable, the cervix shortens (effaces), and the circumference of the proximal end of the cervical canal begins to increase at the internal os. As labor progresses, growth of the cervical diameter propagates to the distal end of the cervical canal, toward the external os. In the final stages of labor, the external os dilates allowing for the unobstructed passage of the fetus.

In addition to the physical and biochemical changes associated with normal labor, genetic or environmental factors, such as medical illness or infection, stress, malnutrition, chronic deprivation and certain chemicals or drugs can cause changes in the cervix. For example, it is well known that the in utero exposure of some women to diethylstilbestrol (DES) results in cervical abnormalities and in some cases gross anatomical changes, which leads to an incompetent cervix where the cervix matures, softens and painlessly dilates without apparent uterine contractions. An incompetent cervix can also occur where there is a history of cervical injury, as in a previous traumatic delivery, or as a result of induced abortion of the cervix is forcibly dilated to large diameters. Details of the incompetent cervix are discussed in Sonek, et al., *Preterm Birth. Causes, Prevention and Management*, Second Edition, McGraw-Hill, Inc., (1993), Chapter 5, which is incorporated by reference herein.

Cervical incompetence is a well recognized clinical problem. Several investigators have reported evidence of increased cervical os diameter as being consistent with cervical incompetence (see Brook et al., *J. Obstet. Gynecol.* 88:640 (1981); Michaels et al., *Am. J. Obstet. Gynecol.* 154:537 (1986); Sarti et al., *Radiology* 130:417 (1979); and Vaalamo et al., *Acta Obstet. Gynecol. Scan* 62:19 (1983), all of which are incorporated by reference herein). Internal os diameters ranging between 15 mm to 23 mm have been observed in connection with an incompetent cervix. Accordingly, a critical assessment in the diagnosis of an incompetent cervix involves measurement of the internal cervical os diameter.

There are also devices and methods to measure the diameter of the external cervical os. For example, cervical diameter can be manually estimated by a practitioner's use of his or her digits. Although an individual practitioner can achieve acceptable repeatability using this method, there is significant variation between practitioners due to the subjective nature of the procedure. To address these concerns, various monitoring and measuring devices and methods have been developed. For example, an instrument for measuring dilation of the cervix uteri is described in U.S. Pat. No. 5,658,295. However, this device is somewhat large, leading to a risk of injury to the fundus of the vagina or cervical os. Additionally, it is not disposable and requires repeated sterilization. Another device for measuring cervical diameter is described, for example, in U.S. Pat. No. 6,039,701. In one version, the device described therein has a loop element which is secured to the cervix. The loop expands or contracts with the cervix and a gauge is coupled to the loop for measuring changes in the loop dimension. Such changes can then be detected by electronic means. Accordingly, this device is rather complex and expensive to manufacture.

Even if a woman is found to have an apparently normal internal cervical os diameter, there may nonetheless be a risk for preterm labor and delivery. Currently, risk assessment for preterm delivery remains difficult, particularly among women with no history of preterm birth. However, the findings that preterm delivery is more common among women with premature cervical shortening or effacement suggest that measuring the length of the cervix would be predictive for preterm labor.

Currently, a physician has at least two options to measure the length of the cervix in the fornix vaginae. One such method involves serial digital examination of the cervix by estimating the length from the external cervical os to the cervical-uterine junction, as palpated through the vaginal fornix. Although this is useful for general qualitative analysis, it does not afford an easy nor accurate measurement of the length of the cervix from the external cervical os to the cervical-uterine junction (also described herein as the length of the cervix extending into the vagina) and, therefore, does not provide an accurate assessment of the risk of preterm labor. Despite the use of gloves, vaginal exams always carry with them the risk of transmitting infectious agents, especially to the fetal membranes, the lining and/or muscle of the uterus, or the fetus itself.

Another method involves real-time sonographic evaluation of the cervix. This method provides relatively quick and accurate cervical dimensions. However, it requires expensive equipment, highly skilled operators, as well as skill in interpretation of results, which are all subject to human error. Additionally, there is a risk that the probe that must be inserted into the vagina as part of the procedure may cause injury if not inserted with care. Also, due to the expense of the procedure many women, especially those without proper health insurance, cannot afford to have a sonographic test performed.

It would be beneficial if there were an instrument a practitioner could use to measure the cervix quickly and accurately, and with little material expense. Although there are several instruments available for determining various dimensions of the uterus, there is no suitable instrument for measuring the length of the cervix in the fornix vaginae. For example, U.S. Pat. No. 4,016,867 describes a uterine caliper and depth gauge for taking a variety of uterine measurements, which although useful for fitting an intrauterine contraceptive device, is not capable of measuring the length of the cervix in the fornix vaginae due to interference by the caliper's wings. In fact, similar devices described in U.S. Pat. Nos.: 4,224,951; 4,489,732; 4,685,747; and 5,658,295 suffer from similar problems due to their use of expandable wings or divergable probe tips. These devices are also relatively sophisticated, making them expensive to manufacture and purchase. U.S. Pat. No. 3,630,190 describes a flexible intrauterine probe, which is particularly adapted to measuring the distance between the cervical os and the fundus of the uterus. The stem portion of the device has a plurality of annular ridges spaced apart from each other by a predetermined distance, preferably not more than one-half inch apart. However, this device is not adapted for accurately measuring the length of the cervix in the fornix vaginae because of the lack of an appropriate measuring scale and a slidable indicator for automatically recording the measurement.

Accordingly, there is currently no commercially available, quick, inexpensive as well as accurate device to assess the risk of preterm labor by measuring the length of the cervix in the fornix vaginae. Therefore, many women at risk for preterm labor may be unaware of the risk to their pregnancy and their unborn child. If such a device were available, many more women would be better informed about the course of their pregnancy and would then be able to make better choices about becoming pregnant at all, or about managing their pregnancy to reduce the risk of preterm labor and injury to the unborn child.

Thus, there exists a need for a simple and inexpensive device that can be used to determine the length of the cervix in the fornix vaginae and, thus, predict the risk of preterm labor, as well as other conditions. There is also a need for such a device that can measure the dilation of the cervix uteri, to provide an overall assessment of the cervix and to determine the particular stage of labor. Ideally, the device should be adapted for use by a physician or obstetrician or even a trained nurse in the doctor's office or clinic. Preferably, the device should be sterile and disposable. In addition, it is desirable that device record the measurement automatically. The present invention satisfies these needs and provides related advantages as well.

SUMMARY OF THE INVENTION

The present invention provides a device for determining a dimension of a female reproductive organ. The device has an elongated member having a distal region and a proximal region, and a slidable indicator slidably engaged with the elongated member on the distal region. The slidable indicator has a surface adapted to contact the reproductive organ when the distal region of the elongated member is inserted thereinto. In additional embodiments, there is a measuring scale disposed on the elongated member, the elongated member is made of plastic, the distal region has an end formed for non-abrasive contact with a tissue and the elongated member has a hand grip. Preferably, the dimension of the female reproductive organ is the length of the cervix in the fornix vaginae.

The invention also provides a device for determining the length of the cervix in the fornix vaginae. The device has an elongated member having a distal region and a proximal region, and a slidable indicator slidably engaged with the elongated member on the distal region. The slidable indicator has a surface adapted to contact the reproductive organ when the distal region of the elongated member is inserted thereinto. In additional embodiments, there is a measuring scale disposed on the elongated member, the elongated member is made of plastic, the distal region has an end formed for non-abrasive contact with a tissue and the elongated member has a hand grip.

The invention further provides a device for determining a dimension of the fornix vaginae. The device has an elongated member having a distal region and a proximal region, and a slidable indicator slidably engaged with the elongated member on the distal region. The slidable indicator has a surface adapted to contact the reproductive organ when the distal region of the elongated member is inserted thereinto. In additional embodiments, there is a measuring scale disposed on the elongated member, the elongated member is made of plastic, the distal region has an end formed for non-abrasive contact with a tissue and the elongated member has a hand grip.

The invention also provides a device for determining the depth of the uterus. The device has an elongated member having a distal region and a proximal region, a measuring scale on the distal region of the elongated member, and a slidable indicator slidably engaged with the elongated member on the distal region. The slidable indicator has a surface adapted to contact the cervix when the distal region of the elongated member is inserted into the vagina. Additional embodiments of the device are made of plastic, the distal region of the elongated member has an end formed for non-abrasive contact with a tissue, and the proximal region of the elongated member has a hand grip.

The invention further provides a device for measuring the dilation of cervix uteri. The device has an elongated member having a distal region, a proximal region and a bend in the elongated member at or near the distal region such that the distal region and the proximal region are approximately perpendicular to one another. The device also has a measuring scale on the distal region of the elongated member and a slidable indicator slidably engaged with the elongated member on the distal region. The slidable indicator has a surface adapted to contact the cervix when the distal region of the elongated member is inserted into the vagina. Additional embodiments of the device are made of plastic, the distal region of the elongated member has an end formed for non-abrasive contact with a tissue, and the proximal region of the elongated member has a hand grip.

The invention also provides a device for determining a dimension of a female reproductive organ comprising a hollow member, an elongated member insertable within the hollow member, and a slidable indicator slidably engaged to the proximal region of the elongated member. The proximal region of the elongated member preferably includes a measuring scale. As the elongated member is advanced distally through the hollow member, the slidable indicator slides along the measuring scale, thereby providing a measurement for the desired dimension of the female reproductive organ. In addition, the distal region of the elongated member may also include a measuring scale. Unidirectional detents may be provided on the measuring scale located on the proximal region in order to provide locking mechanisms to prevent unwanted movement of the slidable indicator. An observation window may be provided towards the distal end of the hollow member to facilitate visual observation of the elongated member as it travels within the lumen of the hollow member. Additionally, a hand grip may be positioned on the proximal end of the elongated member to facilitate manipulation of the device.

The invention also provides methods using the devices disclosed herein. For example, the invention provides a method for predicting the risk of preterm labor in an individual by the steps of inserting into the vagina a device comprising an elongated member having a distal region and a proximal region, and a slidable indicator slidably engaged with the elongated member on the distal region, and the slidable indicator has a surface adapted to contact the cervix when the distal region of the elongated member is inserted into the vagina; until the slidable indicator contacts the cervix and the distal region contacts the cervical-uterine junction at the fornix vaginae; and determining the length of the cervix in the fornix vaginae by observing the position of the slidable indicator along said elongated member, wherein the length of the cervix in the fornix vaginae is inversely related to the risk of preterm labor.

The invention also provides a method for predicting the risk of miscarriage in an individual by the steps of: inserting into the vagina a device having an elongated member having a distal region and a proximal region, and a slidable indicator slidably engaged with the elongated member on the distal region, and the slidable indicator has a surface adapted to contact the cervix when the distal region of the elongated member is inserted into the vagina, until the slidable indicator contacts the cervix and the distal region contacts the cervical-uterine junction at the fornix vaginae; and determining the length of the cervix in the fornix vaginae by observing the position of the slidable indicator along the elongated member, wherein the length of the cervix in the fornix vaginae is inversely related to the risk of miscarriage.

The invention also provides a method for predicting the ease of inducing labor in an individual by the steps of: inserting into the vagina a device having an elongated member having a distal region and a proximal region, and a slidable indicator slidably engaged with the elongated member on the distal region, and the slidable indicator has a surface adapted to contact the cervix when the distal region of the elongated member is inserted into the vagina, until the slidable indicator contacts the cervix and the distal region contacts the cervical-uterine junction at the fornix vaginae; and determining the length of the cervix in the fornix vaginae by observing the position of the slidable indicator along the elongated member, wherein the length of the cervix in the fornix vaginae is inversely related to the ease of inducing labor.

The invention further provides a method for assessing the fertility of an individual by the steps of: inserting into the vagina a device having an elongated member having a distal region and a proximal region, and a slidable indicator slidably engaged with the elongated member on the distal region, and the slidable indicator has a surface adapted to contact the cervix when the distal region of the elongated member is inserted into the vagina, until the slidable indicator contacts the cervix and the distal region contacts the cervical-uterine junction at the fornix vaginae; and determining the length of the cervix in the fornix by observing the position of the slidable indicator along the elongated member, wherein the length of the cervix in the fornix vaginae is inversely related to the fertility of an individual.

In addition, the invention provides methods for measuring the dilation of a cervix uteri, where the cervix uteri comprises one side and an opposite side, the method comprising, inserting into the vagina a device comprising, an elongated member having a distal region, a proximal region, and a bend in the elongated member at or near the distal region such that the distal region and the proximal region are approximately perpendicular to one another; a measuring scale on the distal region of the elongated member; and a slidable indicator slidably engaged with the elongated member on the distal region, the slidable indicator having a surface adapted to contact one side of the cervix uteri when the distal region of the elongated member is inserted into the vagina, until the slidable indicator contacts one side of the cervix uteri at or near the external os; moving the device laterally such that the slidable indicator remains in contact with one side of the cervix uteri at or near the external os and such that the slidable indicator slides along the elongated member until an end of the elongated member at the distal region is in alignment with the opposite side of the cervix uteri at or near the external os; and determining the dilation of the cervix uteri by observing the position of the slidable indicator on the measuring scale on the elongated member.

DESCRIPTION OF THE DRAWINGS

FIG. 6 shows an embodiment of the device with an elongated member adapted for insertion within a hollow member.

FIGS. 7a and 7b show placement of the device illustrated in FIG. 6 to determine the length of the cervix.

FIGS. 14a and 14b illustrate embodiments of the device with an elongated member characterized by a distal end of increased surface area.

DETAILED DESCRIPTION

The present invention provides various devices and methods for determining dimensions of female reproductive organs. For example, the device is particularly adapted for determining the length of the cervix in the fornix vaginae, which, as described above, is related to the risk of preterm labor in an individual. The device is also suited for determining the dilation of the cervix uteri, for predicting the risk of preterm labor or the particular stage of delivery. However, it is contemplated herein, and also understood by those skilled in the art that the invention can be used not only for determining various dimensions of female reproductive organs, but for determining the dimension of any body cavity or passageway where such a device would be insertable, such as a vagina, uterus, mouth, throat, nasal cavity, ear channel, rectum, and also to any cavity created and opened by surgery, for example, during chest, abdominal or brain surgery. The device is also preferably fabricated from inexpensive materials and the measurement is quick to perform. Thus it allows the practitioner to repeat the test over time and therefore to more closely monitor a woman's pregnancy and risk for preterm labor. It is also contemplated that the device record the various measurements automatically, where the only input required by the practitioner is the proper insertion of the device into the body cavity or passageway. This is accomplished by the use of the slidable indicator.

Figure 1:
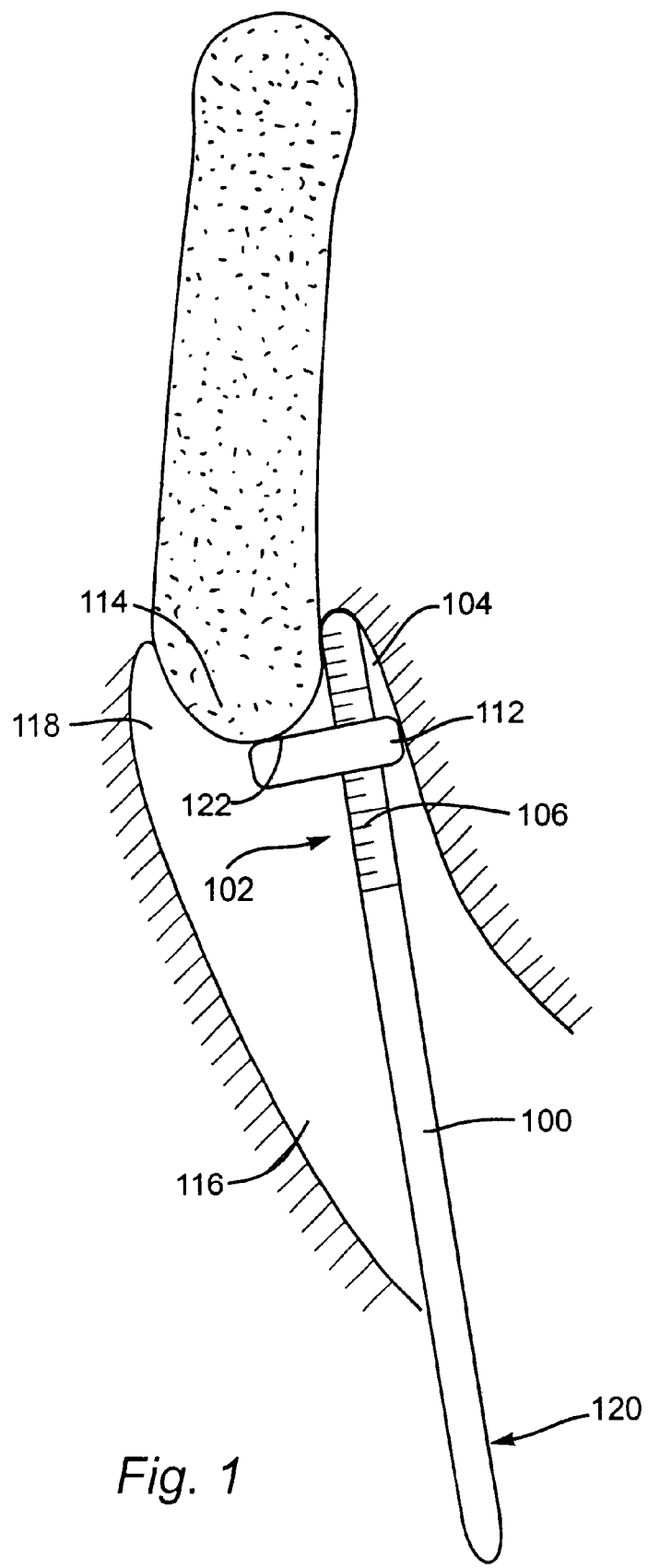
FIG. 1 shows a side view of the female reproductive system with placement of the device in the anterior fornix at the cervical-uterine junction with the slidable indicator contacting the cervix.

One dimension of a female reproductive organ that the device is adapted for, as shown in FIG. 1, for example, is measuring the length of the cervix 14 in the fornix vaginae 118. As used herein, the term "length of the cervix in the fornix vaginae" refers to and is used interchangeably with "the length of the cervical os to the cervical-uterine junction." Also used herein, the term "fornix vaginae" refers to the recess formed between the vaginal wall and the vaginal part of the cervix. The fornix vaginae may be divided into pars anterior (the anterior fornix), the pars posterior (posterior fornix) and the pars lateralis (lateral fornix), depending on its relation to the walls of the vagina. The device of the invention can be inserted into any of these parts of the fornix vaginae, depending on the choice of the user, to determine either the depth of the fornix vaginae at any particular point, or the length of the cervix in the fornix vaginae.

The device in FIG. 1 for determining a dimension of a female reproductive organ comprises an elongated member 100 having a distal region 102 and a proximal region 120, and a slidable indicator 112 slidably engaged with the elongated member 100 on the distal region 102, said slidable indicator 112 having a surface 122 adapted to contact the reproductive organ when the distal region 102 of the elongated member 100 is inserted thereinto. In order to properly use the device to measure the length of the cervix in the fornix vaginae, the slidable indicator must be initially at or near the distal end of the elongated member so as to be able to contact a body tissue when the distal end of the elongated member is inserted. If the slidable indicator is too far away from the distal end, such as for example at the proximal end, then the slidable indicator will not contact the tissue desired and no measurement will be recorded.

Figure 2:
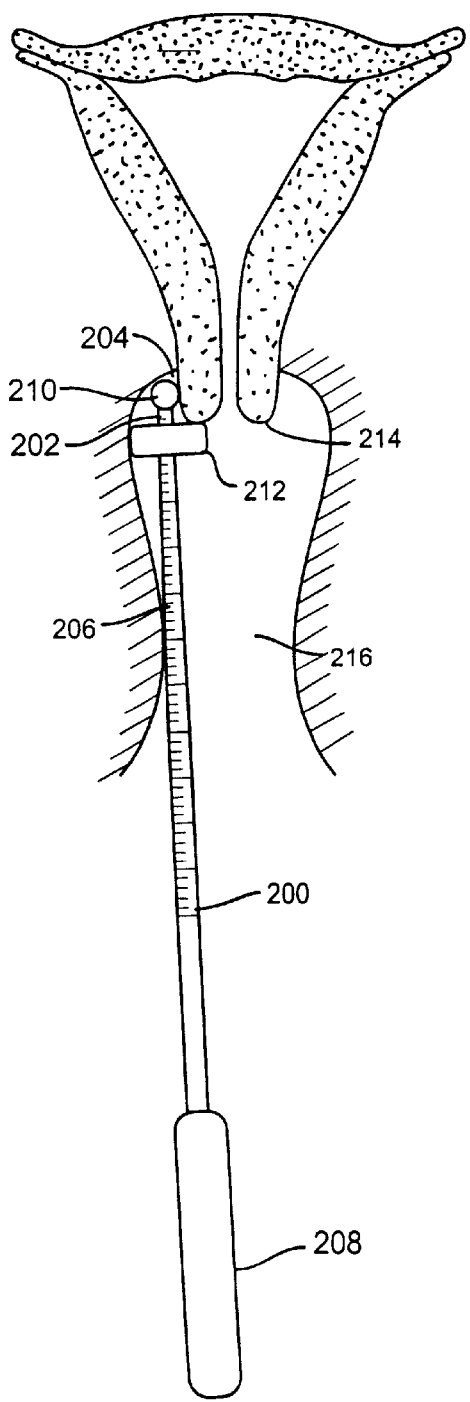
FIG. 2 shows alternative placement of the device in the lateral fornix at the cervical-uterine junction with the slidable indicator contacting the cervix.
Figure 4A:
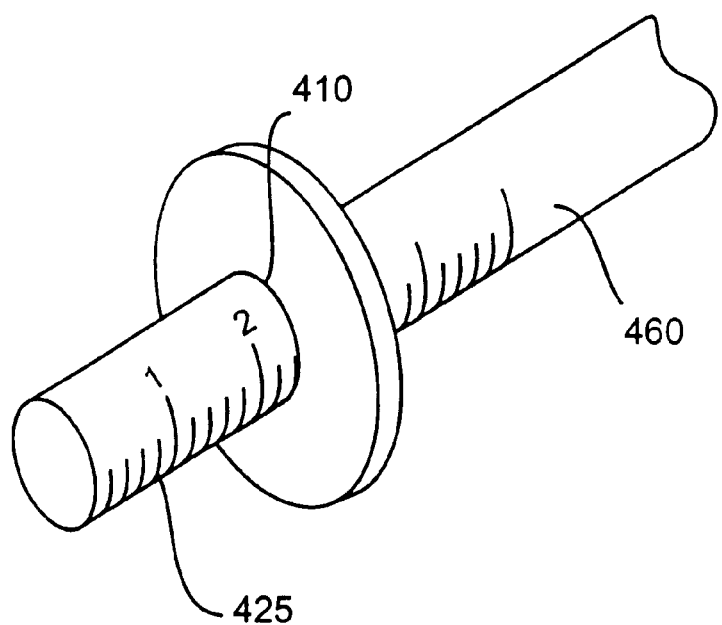
FIG. 4a shows an embodiment of the device with a round elongated member.
Figure 4B:
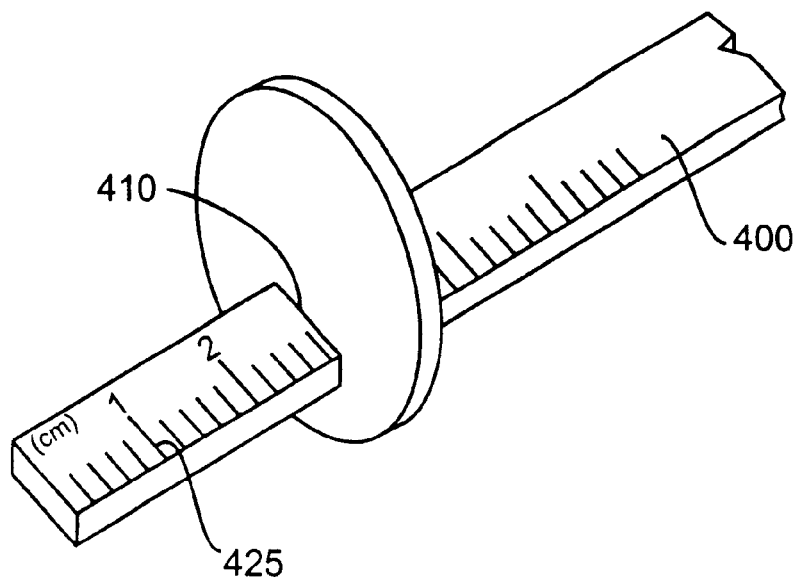
FIG. 4b shows an alternative embodiment of the device with a flat elongated member.

As used herein the "elongated member" comprises a rod, a stick or a strip, which may be flexible or rigid, rectilinear, annular, ovoid or other suitable shapes in cross-section and made from a biologically inert plastic material. One skilled in the art understands that various other cross-sectional shapes are contemplated as well. A round elongated member 410 is seen in FIG. 4a. A flat elongated member 420, which may be a strip, for example, is seen in FIG. 4b. Additionally, the elongated member may be tapered, with a narrower diameter on the distal region and a larger diameter on the proximal region, such that the slidable indicator is prevented from traveling too far down the elongated member in the direction of the proximal end. In any embodiment, preferably the elongated member will be sterile to reduce the risk of infection. Accordingly, the device should be commercially provided in a sealed package. Alternatively, the elongated member can be made from stainless steel if desired. However, the use of biologically inert plastic material or the like significantly reduces costs. Additionally, the elongated member may have an end on the distal region, the end shaped for non-abrasive contact with a tissue. As seen in FIG. 2, for example, this end 210 can comprise a spherical head or nodule or any other non-abrasive shape to reduce irritation and scraping of the cervical canal, fundus of the vagina or perforation of the fundus of the uterus.

As used herein the term "distal region" refers to a region of the elongated member which is adapted to be inserted first into the body cavity of passageway. As such, it will be that part of the device away from the hand of the user. As used herein the term "proximal region" refers to an area or region of the device near the user and can have, if desired, a hand grip.

As seen in FIG. 1, the practitioner can place the device so that the distal region 102 is in the anterior fornix 104. The elongated member 100 has a measuring scale 106, and if desired, although not required, a hand grip or handle on the proximal region 120 (not shown). Preferably, the distal region 102 has an end formed for non-abrasive contact with the tissue. A further example of such an end is a spherical head or nodule. The slidable indicator 112 contacts the end of the cervix 114 and slides along the elongated member 100 as the distal region 102 approaches the anterior fornix 104. The distance between the slidable indicator 112 and the end 110 represents the length of the cervix in the vagina 116.

Alternatively, the practitioner can place the device in the lateral fornix 204, if desired, as shown in FIG. 2. The elongated member 200 preferably has a measuring scale 206, and if desired, although not required, a handle or hand grip 208. Preferably, the distal region 202 has an end 210 formed for non-abrasive contact with the tissue. The slidable indicator 212 contacts the end of the cervix 214 and slides along the elongated member 200 as the distal region 202 approaches the lateral fornix 204. The distance between the slidable indicator 212 and end 210 represents the length of the cervix in the vagina 216.

Preferred embodiments of the device have a measuring scale on the distal region of the elongated member. For example, in FIG. 4a and FIG. 4b, the measuring scale 425 is shown. As used herein, the "measuring scale" refers to any number of a series of visual markings on the elongated member at or near the distal end, which relate a measurement or distance. In a particular preferred embodiment, the measuring scale will provide 1 mm incremental markings along the length of the elongated rod, starting at the distal end such that the markings accurately reflect the length of the elongated member along any point thereof. For example, the first marking would be one millimeter from the end of the end of elongated member and would be marked with a single line indicating 1 mm.

Figure 5:
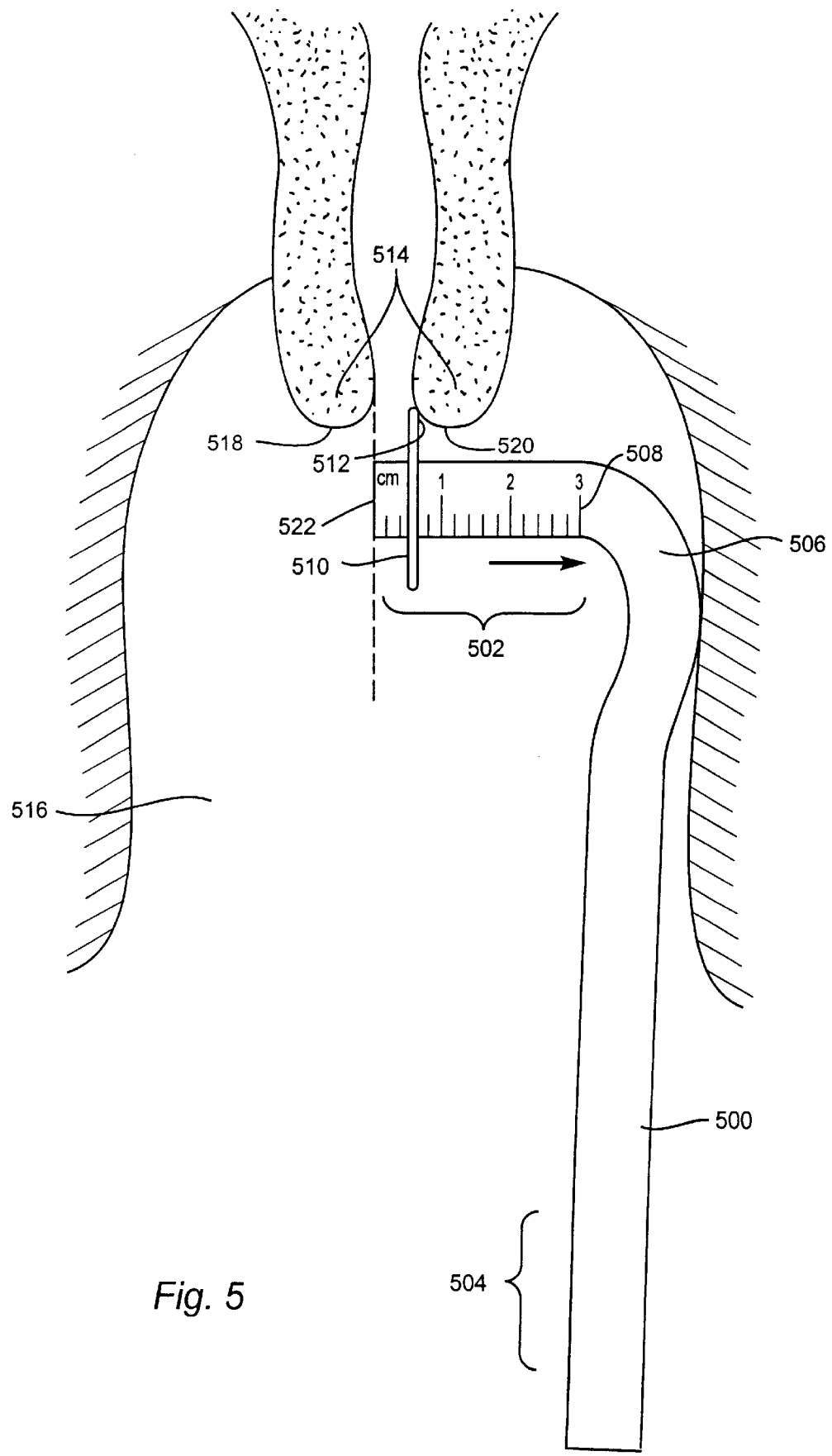
FIG. 5 shows an additional embodiment of the device for determining the dilation of the cervix uteri.

Another dimension of a female reproductive organ that the device is adapted for determining is the dilation of the cervix uteri during pregnancy, during various stages of labor, or even when the female is not pregnant. Traditionally, the dilation of the cervix uteri is used to predict when delivery is imminent. However, the dilation of the cervix uteri may provide an indication of whether a cervix is incompetent, which would be an important consideration to be aware of even before a female becomes pregnant. In this embodiment of the device, seen in FIG. 5, the device comprises an elongated member 500 having a distal region 502 and a proximal region 504, and a bend or turn 506 in the elongated member 500 at or near the distal region 502 such that the distal region 502 and the proximal region 504 are approximately perpendicular to one another. The device also preferably has a measuring scale 508 on the distal region 502 of the elongated member 500 and a slidable indicator 510 slidably engaged with the elongated member 500 on the distal region 502, the slidable indicator 510 having a surface 512 adapted to contact the cervix uteri 514 when the elongated member 500 is inserted into the vagina 516. Although the use of a bend in the elongated member is preferred, one skilled in the art understands that the elongated member may comprise any suitable shape which allows the dilation of the cervix uteri to be determined. For example, the elongated member may merely be flexible enough to allow the distal end to contact one side of the cervix uteri and the slidable indicator to contact the other side of the cervix uteri, thereby affording a measurement of the dilation of the cervix.

As used herein, the term "cervix uteri" refers to the neck of the uterus, or the lower and narrow end of the uterus between the isthmus and the ostium uteri. In the cross-sectional view of the cervix uteri 514 shown in FIG. 5 for example, the cervix uteri 514 comprises a left side 518 and a right (or opposite) side 520.

In this embodiment of the device, the slidable indicator 510 is initially placed away from the distal region 502 and near the bend 506. The distal region 502 of the elongated member 500 is inserted into the vagina until a surface of the slidable indicator 510 contacts the right side 520 of cervix uteri 514, for example. (If desired, the slidable indicator 510 can alternatively be placed into contact with the left side 518 of the cervix uteri 514.) The practitioner then moves the elongated member 500 laterally, in the direction of the arrow in FIG. 5, such that the slidable indicator 510 remains in contact with the right side 520 and also such that the slidable indicator 510 slides along the measuring scale 508. When the end 522 of the distal region 502 is lined up with the left side 518 of the cervix uteri 514, (shown by a dashed line in FIG. 5), the position of the slidable indicator 510 is observed and the measurement of the dilation of the cervix uteri 514 is obtained.

Figure 3:
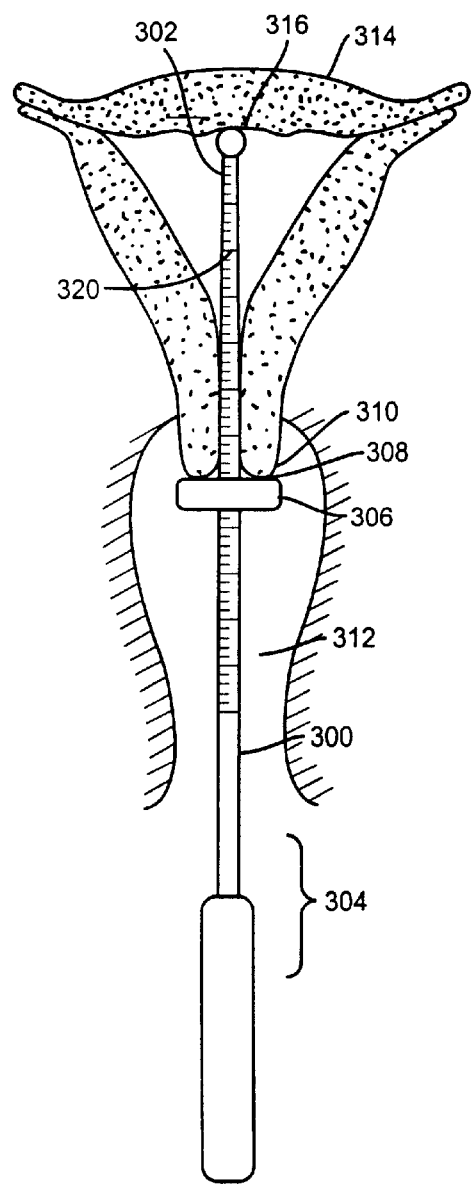
FIG. 3 shows placement of the device to determine the depth of the uterus.

Additionally, the device may be adapted for determining the depth of the uterus as seen in FIG. 3, which is particularly useful, for example, in fitting an intrauterine contraceptive device, where a measurement of the inner dimensions of the uterus are desired. In this embodiment, the device comprises an elongated member 300 having a distal region 302 and a proximal region 304, and a slidable indicator 306 slidably engaged with the elongated member 300 on the distal region 302, the slidable indicator 306 having a surface 308 adapted to contact the cervix 310 when the elongated member 300 is inserted into the vagina 312. As seen in FIG. 3, the distal region 302 of the elongated member 300 is inserted into the uterus 314 until resistance caused by contact of the end of the elongated member 300 on the fundus 316 of the uterus 314 is felt by the user. During the insertion the slidable indicator 306 has already contacted the opening of the cervix 310 and resistance from the cervix 310 causes the slidable indicator 306 to slide along the elongated member 300 as the elongated member 300 is inserted farther into the uterus 314. Accordingly, when the user removes the device, the position of the slidable indicator 306 along the measuring scale 320 provides an accurate measurement of the depth of the uterus 314.

As used herein, the term "depth of the uterus" refers to the distance between the end of the cervix in the vagina and the fundus of the uterus at a point farthest above the cervical canal. A practitioner would desire to determine the depth of the uterus for fabrication of an intrauterine contraceptive device, for example.

As used herein the term "slidably engaged" refers to the particular form of attachment of the slidable indicator to the elongated member. Any form of attachment is contemplated provided that the slidable indicator is allowed to move along the elongated member with less resistance than would otherwise cause deformation of the cervix or any body cavity that it contacts, and while at the same time ensuring that the slidable indicator does not become disengaged, or fall off of the elongated member. As shown in FIGS. 4a and 4b, a hole 410 is formed in the slidable indicator, the hole being sized to slidably engage or fit along the elongated member. In FIG. 4a, the hole 410 is round, since the elongated member 400 is round or annular in cross-section. In FIG. 4b, the hole 410 is rectilinear, since the elongated member 400 is rectilinear.

Preferably, the slidable indicator will be a rounded shape suitably large enough for contacting the end of the cervix in the vaginal space, without being too large to fit into the vagina or into the fornix vaginae. However, one skilled in the art understands that the slidable indicator may be any other suitable shape, such as rectilinear, square or the like. A rounded shape is preferred in order to minimize injury to the surrounding tissues. Also preferably, the slidable indicator will be larger than the external cervical os, thereby preventing it from entering the cervical canal. One skilled in the art understands that any other shape or size of the slidable indicator may be used instead, for example a bar or a rod, so long as it is able to contact the cervix or other body tissue. Also in a preferred embodiment, the slidable indicator will be made from a biologically inert plastic material, like the elongated member.

Turning now to FIG. 6, FIG. 6 illustrates a device 600 for measuring a dimension of a female reproductive organ that includes an elongated member 602 adapted to be positioned within a hollow member 604. The elongated member 602 has a distal region 606 and a proximal region 608. The hollow member 604 includes a distal opening 610, a proximal opening 612, and a lumen 614. A slidable indicator 616 is slidably engaged on the proximal region 608 of the elongated member 602 and outside of the hollow member 604.

In a preferred embodiment, a measuring scale 618 is located on the proximal region 608. The measuring scale 618 is preferably comprised of a plurality of incremental markings 619 corresponding to the individual units of measure for which the device 600 is calibrated. The measuring scale 618 may be calibrated for any measurement system, such as, e.g., metric or English units of measure. As illustrated in FIG. 6, the incremental markings 619 of the measuring scale 618 are located on one side of the proximal region 608. In other embodiments, the markings 619 of the measuring scale 618 may appear on two sides of the proximal region 608, or may extend completely around the circumference of the proximal region 608. In another embodiment of the device 600, the measuring scale 618 will provide 1 mm incremental markings 619 along the length of the elongated member 602. On the device 600, the markings 619 start at the proximal end of the elongated member 602 and proceed distally, such that the markings 619 accurately reflect the length of the elongated member 602 along any point thereof. For instance, the first marking 619 would be one millimeter from the end of the proximal end of the elongated member 602 and would be marked with a single line indicating 1 mm.

In another embodiment, a color coded incremental marking is used to indicate the 25 mm point along the measuring scale 618. For example, a red or other brightly colored incremental marking may be used. Utilizing a color coded incremental marking to designate the 25 mm point is desirably since, for example, a cervix length less than 25 mm indicates that the subject has a much greater risk for preterm delivery than a subject whose cervix is greater than 25 mm in length.

To operate the device 600, the elongated member 602 is positioned within the lumen 614 of the hollow member 604 with the slidable indicator 616 slidably engaged to the proximal region 608 of the elongated member 602. Additionally, the slidable indicator 616 is located proximal from the proximal opening 612 of the hollow member 604. The elongated member 602 is then advanced through the lumen 614 distally towards the distal opening 610 of the hollow member 604. As the elongated member 602 is advanced, the slidable indicator 616 will contact the proximal end of the hollow member 604 at the proximal opening 612. The slidable indicator 616 is characterized by a diameter that is either the same as or larger than the outer diameter of the hollow member 604. As a result, after the slidable indicator 616 comes in contact with the proximal opening 612 of the hollow member 604, the slidable indicator 616 does not advance with the elongated member 602 as the elongated member 602 moves distally in the lumen 614.

Turning now to FIGS. 7a and 7b, the device 600 is illustrated as it will preferably be positioned within the vagina 116 in order to measure the length of the cervix 114. The distal opening 610 of the hollow member 604 is adapted to simultaneously contact a proximal surface of the cervix 114 and a wall of the vagina 116, such as, e.g., a wall of the fornix vaginae 118. This configuration enables the elongated member 602 to travel distally through the lumen 614 of the hollow member 604, through the distal opening 610 and into, for example, the fornix vaginae 118. The distal region 606 of the elongated member 602 preferably has an end formed for non-abrasive contact with body tissue. The end may be, for example, a spherical head or a nodule.

In one embodiment, the measuring scale 618 is disposed on the proximal region 608 such that the most distally located incremental marking 619 of the measuring scale 618 is oriented at the proximal opening 612 of the hollow member 604 when the most distal surface of the distal region 606 of the elongated member 602 is oriented at the distal opening 610 of the hollow member 604. Also, the slidable indicator 616 is positioned along the elongated member 606 at the proximal opening 612 of the hollow member 604. As the elongated member 606 is advanced distally through the lumen 614 of the hollow member 604, and as the slidable indicator 616 is prevented from moving distally by the proximal opening 612 of the hollow member 604, the measuring scale 618 slides past the slidable indicator 616 as the elongated member 606 advances. The elongated member 602 stops advancing distally through the lumen 614 once the distal end of the distal region 606 comes into contact with an opposing surface in the body, such as, e.g., the extreme distal wall of the fornix vaginae 118 (typically the reflection of the cervico-vagino/uterine junction either anteriorly or posteriorly). When the elongated member 602 is prevented from further advancing, the length 622 of the cervix 114 is capable of being measured by reading the position of the slidable indicator 616 on the measuring scale 618. For example, in the embodiment illustrated in FIG. 7a and 7b, the distance 620 between the most distal incremental marking 619 of the measuring scale 618 and the slidable indicator 616 is approximately equivalent to the length 622 of the cervix 114.

Figure 8A:
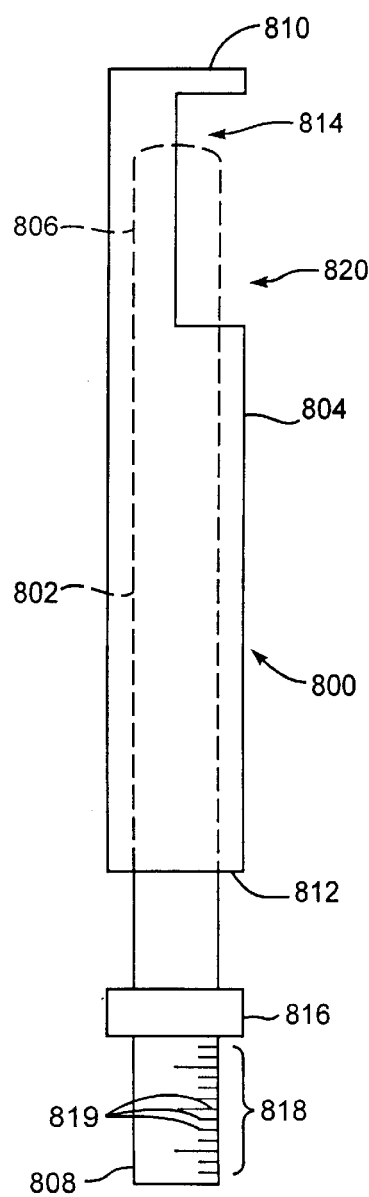
FIG. 8a shows an embodiment of the device with an elongated member adapted for insertion within a hollow member that further includes an observation opening disposed towards the distal end of the hollow member.

Turning now to FIG. 8a, a device 800 for measuring a dimension of a female reproductive organ comprising a hollow member 804, an elongated member 802, and a slidable indicator 816 is illustrated, wherein the hollow member 804 includes an observation opening 820. The elongated member 802 has a distal region 806 and a proximal region 808. The hollow member 804 includes a distal opening 810, a proximal opening 812, and a lumen 814. The hollow member 804 further comprises an observation opening 820 located towards the distal opening 810. The observation opening 820 allows for visual confirmation of the progression of the elongated member 802 through the lumen 814 of the hollow member 804, as the elongated member 802 is advanced distally through the lumen 814. A slidable indicator 816 is slidably engaged on the proximal region 808 of the elongated member 802 and outside of the hollow member 804.

In a preferred embodiment, a measuring scale 818 is located on the proximal region 808. The measuring scale 818 is preferably comprised of a plurality of incremental markings 819 corresponding to the individual units of measure for which the device 800 is calibrated. Additionally, the measuring scale 818 is calibrated and positioned in the same manner as the measuring scale 618 on device 600, which is illustrated in FIG. 6. For purposes of brevity, reference is made to the description of the measuring scale 618 on device 600, as such description also applies to the measuring scale 818 on device 800.

To operate the device 800, the elongated member 802 is positioned within the lumen 814 of the hollow member 804 with the slidable indicator 816 slidably engaged to the proximal region 808 of the elongated member 802. Additionally, the slidable indicator 816 is located proximal from the proximal opening 812 of the hollow member 802, The elongated member 802 is then advanced through the lumen 814 distally towards the distal opening 810 of the hollow member 804. As the elongated member 802 is advanced, the slidable indicator 816 will contact the proximal end of the hollow member 804 at the proximal opening 812. The slidable indicator 816 is characterized by a diameter that is either the same as or larger than the diameter of the hollow member 804. As a result, after the slidable indicator 816 comes in contact with the proximal opening 812 of the hollow member 804, the slidable indicator 816 does not advance with the elongated member 802 as the elongated member 802 moves distally in the lumen 814.

As shown in FIG. 8a, device 800 further includes an observation opening 820 positioned distally on the hollow member 804. The observation opening 820 facilitates visual confirmation of the elongated member 802 as the member 802 is advanced through the lumen 814. Visual confirmation is desirable if, for example, the progression of the elongated member 802 through the lumen 814 is inexplicably prevented, particularly if the distal region 806 of the elongated member 802 is still within the lumen 814. In that event, the observation opening 820 allows for visual confirmation of the positioning of the elongated member 802 within the lumen 814, thereby allowing for any necessary adjustment of the positioning of the elongated member 802 to enable the continued advancement of the member 802 through the hollow member 804. The observation opening 820 may also be implemented in any of the other embodiments of a device with an elongated member insertable within a hollow member to facilitate visual confirmation of the position of the elongated member within the hollow member.

Figure 8B:
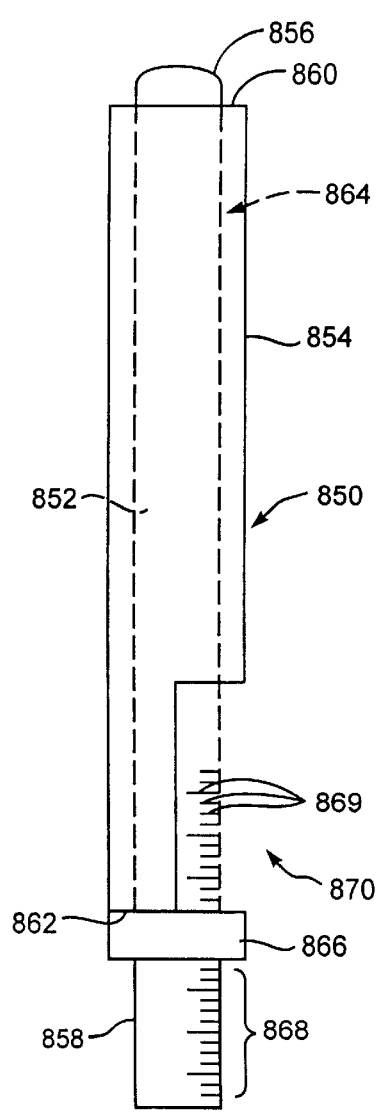
FIG. 8b illustrates an embodiment of the device with an elongated member adapted for insertion within a hollow member that includes an observation opening disposed towards the proximal end of the hollow member.

Turning to FIG. 8b, a device 850 for measuring a dimension of a female reproductive organ comprising a hollow member 854, an elongated member 852, and a slidable indicator 866 is illustrated, wherein the hollow member 854 includes an observation opening 870 located proximally on the hollow member 854. The elongated member 852 has a distal region 856 and a proximal region 858. The hollow member 854 includes a distal opening 860, a proximal opening 862, and a lumen 864. The hollow member 854 further comprises an observation opening 870 located towards the proximal opening 862. A slidable indicator 866 is slidably engaged on the proximal region 868 of the elongated member 852 and outside of the hollow member 854. In a preferred embodiment, a measuring scale 868 is located on the proximal region 858. The measuring scale 868 is preferably comprised of a plurality of incremental markings 869 corresponding to the individual units of measure for which the device 850 is calibrated. Additionally, the measuring scale 868 is calibrated and positioned in the same manner as the measuring scale 818 on device 800, which is illustrated in FIG. 8a. For purposes of brevity, reference is made to the description of the measuring scale 818 on device 800, as such description also applies to the measuring scale 868 on device 850.

The operation of device 800 shown in FIG. 8a is substantially similar, and is applicable, to the operation of device 850 illustrated in FIG. 8b. Consequently, for purposes of brevity, for a detailed description of the operation of device 850, reference is made to the description of the operation of device 800.

As shown in FIG. 8b, device 850 further includes an observation opening 870 positioned proximally on the hollow member 854. In device 850, as with device 800 illustrated in FIG. 8a, the observation opening 870 allows for visual confirmation of the progression of the elongated member 852 through the lumen 864 of the hollow member 854, as the elongated member 852 is advanced distally through the lumen 864. With device 850, however, the observation opening 870 further enables a user to read the position of the slidable indicator 866 along a portion of the measuring scale 868 that would otherwise be hidden from view while the elongated member 852 is still disposed within the lumen 864 of the hollow member 854.

Figure 8C:
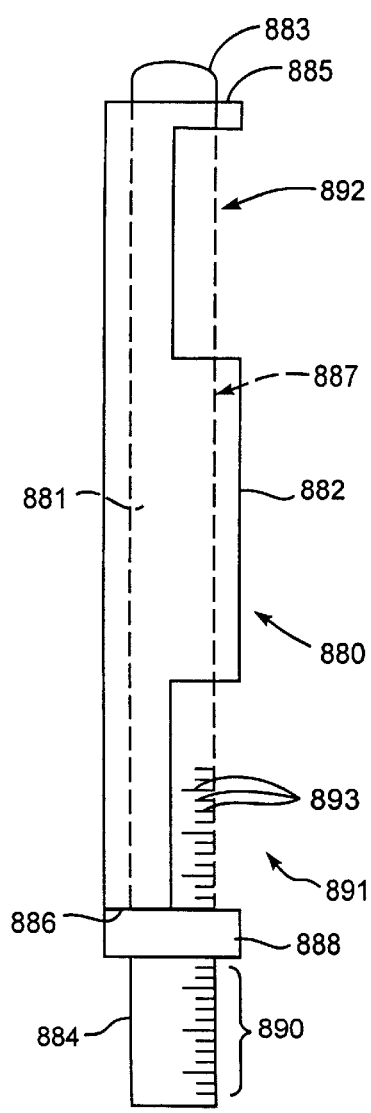
FIG. 8c illustrates an embodiment of the device with an elongated member adapted for insertion within a hollow member that includes a first and second observation openings located on the proximal and distal ends, respectively, of the hollow member.

Turning to FIG. 8c, a device 880 for measuring a dimension of a female reproductive organ comprising a hollow member 882, an elongated member 881, and a slidable indicator 888 is illustrated. The hollow member 884 of the device 880 includes a first observation opening 891 located proximally on the hollow member 884 as well as a second observation opening 892 located distally on the hollow member 884. The elongated member 881 has a distal region 883 and a proximal region 884. The hollow member 882 includes a distal opening 885, a proximal opening 886, and a lumen 887. As previously described, the hollow member 882 further comprises a first observation opening 891 located towards the proximal opening 885 and a second observation opening 892 located towards the distal opening 885. A slidable indicator 888 is slidably engaged on the proximal region 884 of the elongated member 881 and outside of the hollow member 882. In a preferred embodiment, a measuring scale 890 is located on the proximal region 884. The measuring scale 890 is preferably comprised of a plurality of incremental markings 893 corresponding to the individual units of measure for which the device 880 is calibrated. Additionally, the measuring scale 890 is calibrated and positioned in the same manner as the measuring scale 818 on device 800, which is illustrated in FIG. 8a. For purposes of brevity, reference is made to the description of the measuring scale 818 on device 800, as such description also applies to the measuring scale 890 on device 880.

The operation of device 800 shown in FIG. 8a is substantially similar, and is applicable, to the operation of device 880 illustrated in FIG. 8c. Consequently, for purposes of brevity, for a detailed description of the operation of device 880, reference is made to the description of the operation of device 800.

As shown in FIG. 8c, device 880 further includes a first observation opening 891 positioned proximally on the hollow member 882 and a second observation opening 892 positioned distally on the hollow member 882. The observation openings 891 and 892 allow for visual confirmation of the progression of the elongated member 891 through the lumen 887 of the hollow member 882, as the elongated member 881 is advanced from a proximal position distally through the lumen 887. As with the observation opening 870 of device 850 shown in FIG. 8b, the first observation opening 891 enables a user to read the position of the slidable indicator 888 along a portion of the measuring scale 890 that would otherwise be hidden from view while the elongated member 881 is still disposed within the lumen 887 of the hollow member 882.

Figures 9A, 9B, 9C:
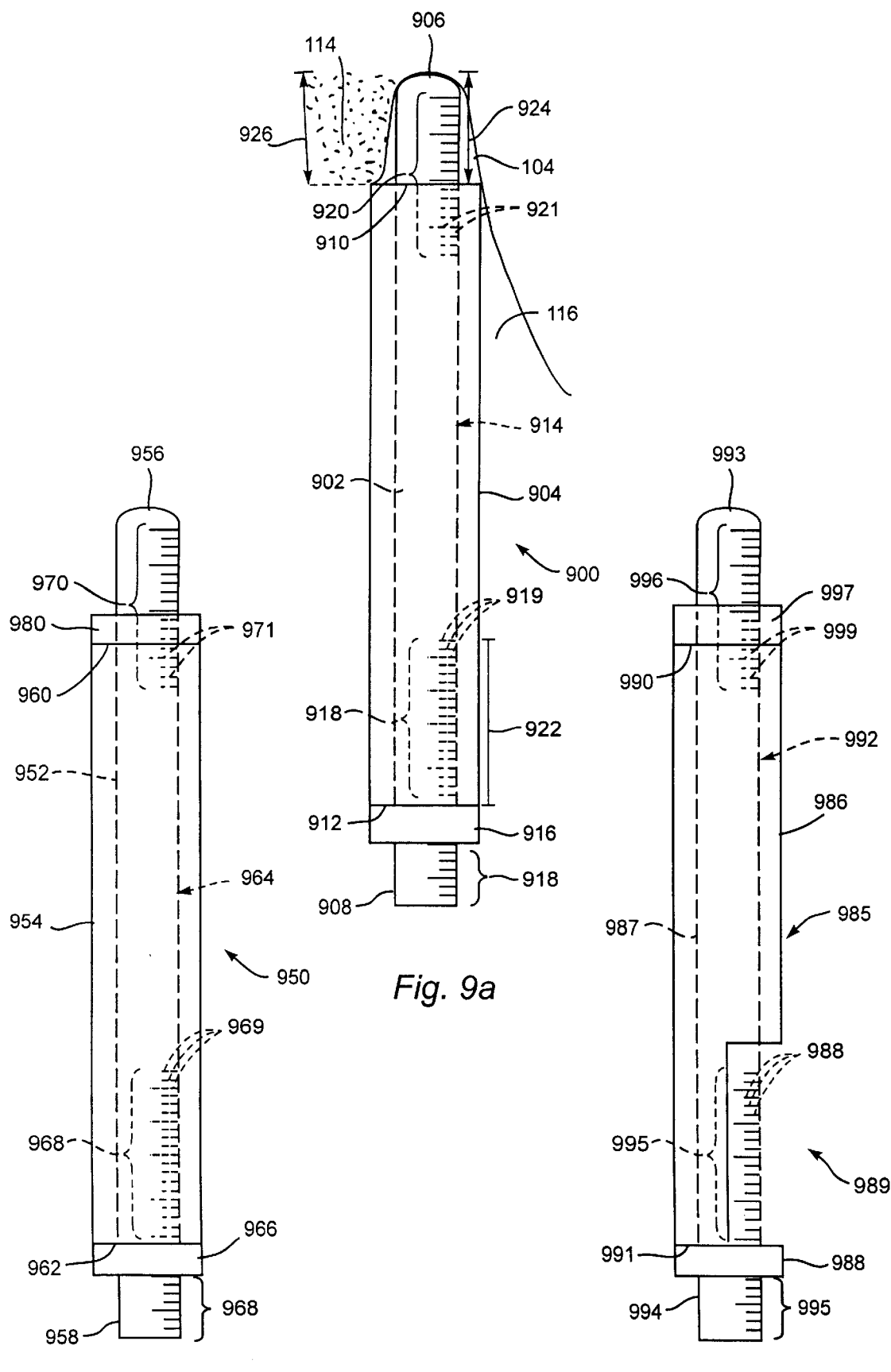
FIG. 9a shows an embodiment of the device with an elongated member adapted for insertion within a hollow member, wherein the elongated member has a first and second measurement scale.
FIG. 9b illustrates an embodiment of the device with an elongated member adapted for insertion within a hollow member, the elongate member having a first and second measurement scale and a first and second slidable indicator engaged on those scales.
FIG. 9c illustrates an embodiment of the device with an elongated member adapted for insertion within a hollow member with an observation opening, the elongate member having a first and second measurement scale, and a first and second slidable indicator.

Illustrated in FIG. 9a is a device 900 for measuring a dimension of a female reproductive organ comprising a hollow member 904, an elongated member 902, and a slidable indicator 916, wherein the elongated member 902 includes two measuring scales located on opposite ends of the member 902. The hollow member 904 includes a distal opening 910, a proximal opening 912, and a lumen 914. The elongated member 902 has a distal region 906 and a proximal region 908. A slidable indicator 916 is slidably engaged on the proximal region 908 of the elongated member 902 and outside of the hollow member 904.

Additionally, the elongated member 902 has a first measuring scale 918 located on the proximal region 908 of the member 902 and a second measuring scale 920 located on the distal region 906 of the member 902. Both the first measuring scale 918 and the second measuring scale 920 are preferably comprised of a plurality of incremental markings 919, 921 respectively, corresponding to the individual units of measure for which the device 900 is calibrated. The measuring scales 918, 920 may be calibrated for any measurement system, such as, e.g., metric or English units of measure. In the embodiment illustrated in FIG. 9a, the incremental markings 919, 921 of the measuring scales 918, 920 are located on one side of the proximal region 908 and distal region 906, respectively. In other embodiments, the markings of the measuring scales 918, 920 may appear on two sides of the proximal region 908 and distal region 906, respectively. In yet another embodiment, the markings 919, 921 of the measuring scales 918, 920 may extend completely around the circumference of the proximal region 908 and distal region 906, respectively. With respect to the incremental markings 919, 921, the measuring scales 918, 920 preferably will provide 1 mm incremental markings 919, 921 along the length of the elongated member 902. On the device 900, the markings 919 for the first measuring scale 918 begin at the proximal end of the elongated member 902 and proceed distally, such that the markings 919 accurately reflect the length of the elongated member 902 along any point thereof. For instance, the first marking would be one millimeter from the end of the proximal end of the elongated member 902 and would be marked with a single line indicating 1 mm. Turning to the markings 921 for the second measuring scale 920, these markings 921 begin at the distal end of the elongated member 902 and proceed proximally, such that the markings 921 accurately reflect the length of the elongated member 902 along any point thereof. As with the markings 919 for the first measuring scale 918, the first marking for the second measuring scale would, for example, be positioned one millimeter from the end of the distal end of the elongated member 902 and would be marked with a single line indicated 1 mm. The presence of a first measuring scale 918 and a second measuring scale 920 on the elongated member 902 of device 900 allow two conforming measurements of a dimension of a female reproductive organ to be obtained, thereby enabling the confirmation of an attempted measurement of the female reproductive organ. In another embodiment, a color coded incremental mark is used for the 25 mm position of either the first or second measuring scale 918, 920, or both of the measuring scales 918, 920. As previously discussed, a cervix length less than 25 mm is indicative of a greatly increased risk for preterm labor. Therefore, a color coded incremental marking at the 25 mm point of either measuring scale would facilitate the detection of an increased risk of preterm labor in a subject by alerting the user or physician of the increased risk associated with a cervix shorter than 25 mm. The color coded, 25 mm incremental marking may be used on one scale alone or on both scales simultaneously.

To operate the device 900, the elongated member 902 is positioned within the lumen 914 of the hollow member 904 with the slidable indicator 916 slidably engaged to the proximal region 908 of the elongated member 902. Additionally, the slidable indicator 916 is located proximal from the proximal opening 912 of the hollow member 902. The elongated member 902 is then advanced through the lumen 914 distally towards the distal opening 910 of the hollow member 904. As the elongated member 902 is advanced, the slidable indicator 916 will contact the proximal end of the hollow member 904 at the proximal opening 912. The slidable indicator 916 is characterized by a diameter that is either the same as or larger than the diameter of the hollow member 904. As a result, after the slidable indicator 916 comes in contact with the proximal opening 912 of the hollow member 904, the slidable indicator 916 does not advance with the elongated member 902 as the elongated member 902 moves distally in the lumen 914. When the elongated member 902 stops advancing distally through the lumen 914 after the distal end of the distal region 906 comes into contact with an opposing surface in the body, such as, e.g., the extreme distal wall of the fornix vaginae 118. When the elongated member 902 is prevented from further advancing into the fornix vaginae 118, the length 926 of the cervix 114 is capable of being measured by reading the two measuring scales 918, 920 either individually or together, i.e., to confirm the veracity of each measurement. First, the position of the slidable indicator 916 on the first measuring scale 918, i.e., the distance 922 between the most distal incremental marking of the first measuring scale 918 and the slidable indicator 916 is approximately equivalent to the length 926 of the cervix 114. Second, the distance 924 from the distal end of the distal region 906 of the elongated member 902 to the distal opening 910 of the hollow member 904 is also approximately equivalent to the length 926 of the cervix 114. In addition to the embodiment illustrated in FIG. 9a, a second measuring scale disposed on the distal region of an elongated member may be used on any of the embodiments of a device that comprises a hollow member and an elongated member insertable within the hollow member.

Turning now to FIG. 9b, a device 950 for measuring a dimension of a female reproductive organ comprising a hollow member 954, an elongated member 952, and a first slidable indicator 966, wherein the elongated member 952 includes two measuring scales located on opposite ends of the member 952, is shown. The hollow member 954 includes a distal opening 960, a proximal opening 962, and a lumen 964. The elongated member 952 has a distal region 956 and a proximal region 958.

The elongated member 952 has a first measuring scale 968 located on the proximal region 958 of the member 952 and a second measuring scale 970 located on the distal region 956 of the member 952. A first slidable indicator 966 is slidably engaged on the proximal region 958 of the elongated member 952 and outside of the hollow member 954. Further, a second slidable indicator 980 is slidably engaged on the distal region 956 of the elongated member 952 and outside of the hollow member 954. Both the first measuring scale 968 and the second measuring scale 970 are preferably comprised of a plurality of incremental markings 969, 971 respectively, corresponding to the individual units of measure for which the device 950 is calibrated. The measuring scales 968, 970 may be calibrated for any measurement system, such as, e.g., metric or English units of measure. In the embodiment illustrated in FIG. 9b, the incremental markings 969, 971 of the measuring scales 968, 970 will be located and calibrated in substantially the same manner as the measuring scales 918 and 920 of device 900 shown in FIG. 9a. For the sake of brevity, reference is made to the descriptions of both the location and calibration of the measuring scales 918 and 920 of device 900 in FIG. 9a as those descriptions are applicable to the incremental markings 969, 971 of the measuring scales 968, 970 of device 950 in FIG. 9b. As with the first and second measuring scales 918, 920 of device 900 in FIG. 9a, the presence of a first measuring scale 968 and a second measuring scale 970 on the elongated member 952 of device 950 allow two conforming measurements of a dimension of a female reproductive organ to be obtained, thereby enabling the confirmation of an attempted measurement of the female reproductive organ.

Device 950 is also operated in substantially the same manner as device 900 illustrated in FIG. 9a. Reference is made to the description of the operation of device 900 as that description applies to the operation of device 950. With device 950, however, the addition of the second slidable indicator 980 allows a user to analyze the measurement of the female reproductive organ by determining the position of the second slidable indicator 980 along the second measuring scale 970, as well as by determining the position of the first slidable indicator 966 along the first measuring scale 968.

Either device 900 or device 950 may further include an observation window located proximally on the hollow members 904, 954, respectively, that enable a user to visually confirm the position of the slidable indicators 916, 966 along a portion of the measuring scales 918, 968 when those portions of the scales 918, 968 would otherwise be obscured from observation, i.e., when the elongated members 902, 952 are still disposed within the lumens 914, 964 of the hollow members 904, 954. Turning now to FIG. 9c, a device 985 for measuring a dimension of a female reproductive organ comprising a hollow member 986, an elongated member 987 including two measuring scales located on opposite ends of the member 987, and a first slidable indicator 988, wherein an observation opening 989 is disposed on the hollow member 986, is shown. The hollow member 986 includes a distal opening 990, a proximal opening 991, and a lumen 992. The elongated member 987 has a distal region 993 and a proximal region 994.

The elongated member 987 has a first measuring scale 995 located on the proximal region 994 of the member 987 and a second measuring scale 996 located on the distal region 993 of the member 987. A first slidable indicator 988 is slidably engaged on the proximal region 994 of the elongated member 987 and outside of the hollow member 986. Further, a second slidable indicator 997 is slidably engaged on the distal region 993 of the elongated member 987 and outside of the hollow member 986. Both the first measuring scale 995 and the second measuring scale 996 are preferably comprised of a plurality of incremental markings 998, 999 respectively, corresponding to the individual units of measure for which the device 985 is calibrated. The measuring scales 995, 996 may be calibrated for any measurement system, such as, e.g., metric or English units of measure. In the embodiment illustrated in FIG. 9c, the incremental markings 998, 999 of the measuring scales 995, 996 will be located and calibrated in substantially the same manner as the measuring scales 968 and 970 of device 950 shown in FIG. 9b. For the sake of brevity, reference is made to the descriptions of both the location and calibration of the measuring scales 968 and 970 of device 950 in FIG. 9b as those descriptions are applicable to the incremental markings 998, 999 of the measuring scales 995, 996 of device 985 in FIG. 9c. As with the first and second measuring scales 968, 970 of device 950 in FIG. 9b, the presence of a first measuring scale 995 and a second measuring scale 996 on the elongated member 987 of device 985 allow two conforming measurements of a dimension of a female reproductive organ to be obtained, thereby enabling the confirmation of an attempted measurement of the female reproductive organ. In addition, the observation opening 989 of device 989 enables a user to determine the position of the slidable indicator 988 along a portion of the first measuring scale 995 while the elongated member 987 is still disposed within the lumen 992 of the hollow member 986.

Device 985 is also operated in substantially the same manner as device 950 illustrated in FIG. 9b. Reference is made to the description of the operation of device 950 as that description applies to the operation of device 985.

It is further noted that an observation opening 989 may also be provided on the device 900 of FIG. 9a to enable a similar determination of the positioning of the slidable indicator 916 along the measuring scale 918 of that device 900. Also, in an alternative embodiment, a device such as device 985 of FIG. 9c further includes a second observation opening located distally on the hollow member to facilitate the visual confirmation of the elongated member through the lumen of the hollow member.

Figures 10, 11, 13:
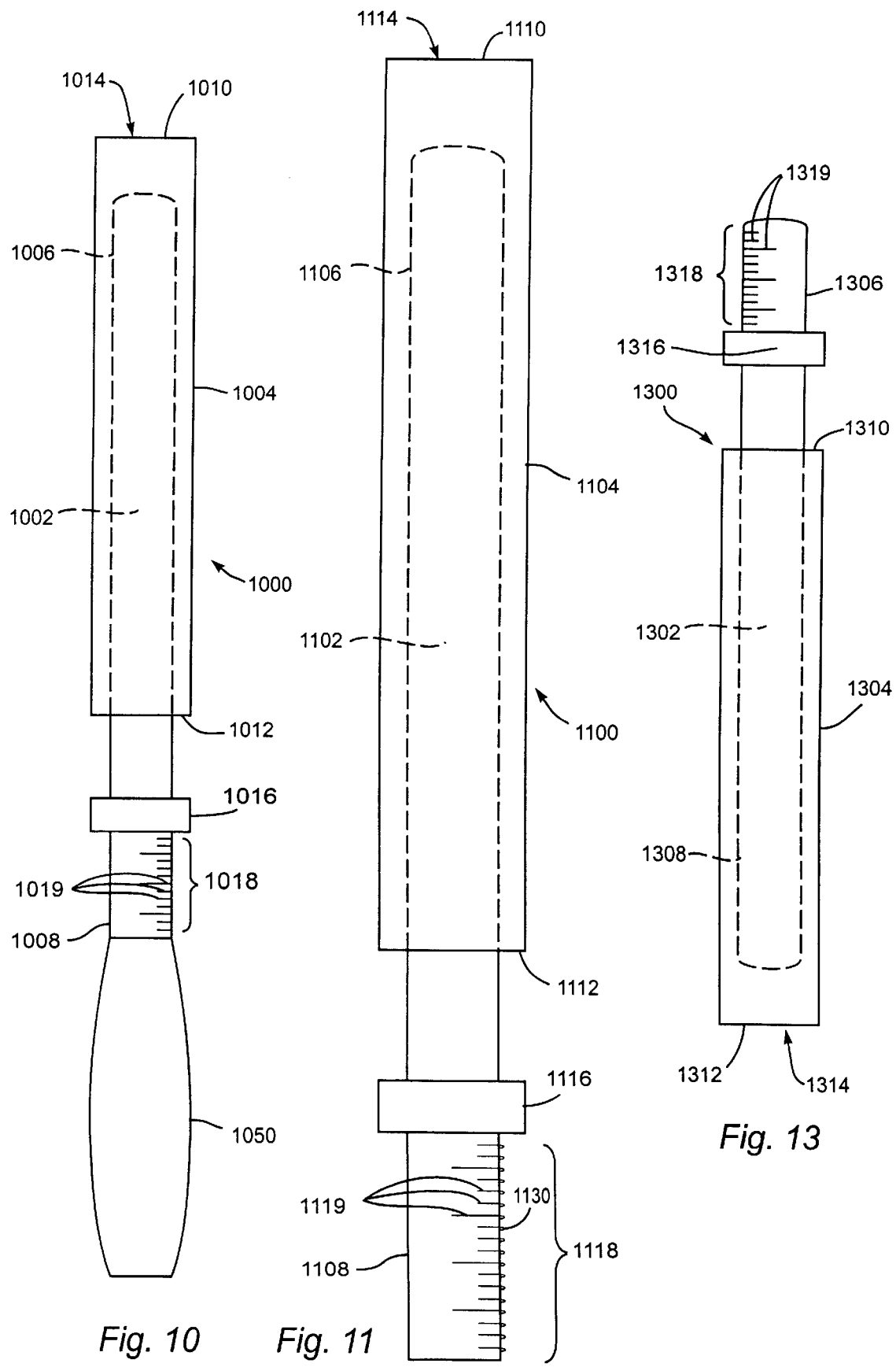
FIG. 10 shows an embodiment of the device with an elongated member, a hollow member, and a hand grip.
FIG. 11 illustrates an embodiment of the device with an elongated member, a hollow member, and unidirectional detents on the measuring scale.
FIG. 13 illustrates an embodiment of the device with an elongated member, a hollow member, and a slidable indicator disposed on the distal region of the elongated member and distally beyond the hollow member.

With any of the embodiments of the devices of the present invention, a hand grip may be provided in order to facilitate the manipulation of the devices. The hand grip is positioned in operable connection with the proximal region of any of the devices and, preferably, is located at the extreme proximal end of the proximal region of a device and also proximally from the measuring scale on the proximal region. Turning to FIG. 10, an exemplary device 1000 for measuring a dimension of a female reproductive organ that includes a hand grip 1050 is shown. The device 1000 comprises an elongated member 1002, with a distal region 1006 and a proximal region 1008, the member 1002 being adapted for positioning within a hollow member 1004. The hollow member 1004 includes a distal opening 1010, a proximal opening 1012, and a lumen 1014. A slidable indicator 1016 is slidably engaged on the proximal region 1008 of the elongated member 1002 and outside of the hollow member 1004. A measuring scale 1018 comprised of a plurality of incremental markings 1019 is disposed on the proximal region 1008 of the elongated member 1002.

The hand grip 1050 is preferably positioned in operable connection with the proximal region 1008 of the elongated member 1002, and, further, on the proximal end of the member 1002. Also, the hand grip 1050 is configured to prevent the slidable indicator 1016 from sliding proximally past the proximal end of the member 1002. For example, the hand grip 1050 is preferably characterized by a diameter that prevents the slidable indicator 1016 from moving beyond the proximal region 1008 of the member 1002. The hand grip 1050 is comprised of any suitable material, such as, e.g., plastic, foam, or rubber. The hand grip 1050 may be manufactured out of the same material as the elongated member 1002 is manufactured or may be manufactured out of a different material. In one embodiment, the hand grip 1050 is color coordinated with the slidable indicator 1016.

Turning now to FIG. 11, a device 1100 for measuring a7 dimension of a female reproductive organ comprising a hollow member 1104, an elongated member 1102, and a slidable indicator 1116 is illustrated. The hollow member 1104 includes a distal opening 1110, a proximal opening 1112, and a lumen 1114. The elongated member 1102 has a distal region 1106 and a proximal region 1108. A slidable indicator 1116 is slidably engaged on the proximal region 1108 of the elongated member 1102 and outside of the hollow member 1104.

Device 1100 further comprises a measuring scale 1118 on the proximal region 1108 of the elongated member 1102 that includes a plurality of unidirectional detents 1130. The measuring scale 1118 is preferably comprised of a plurality of incremental markings 1119 wherein each marking 1119 corresponds the individual units of measure for which the device 1100 is calibrated. In the device 1100 illustrated in FIG. 11, the incremental markings 1119 are located on one side of the proximal region 1108. In other embodiments, the markings 1119 may appear on two opposing sides of the proximal region 1108, or may extend completely around the circumference of the proximal region 1108. The measuring scale 1118 may be calibrated for any measurement system, such as, e.g., metric or English units of measure.

The slidable indicator 1116 is preferably manufactured using a material that is more pliable than the material used to manufacture the elongated member 1102. More specifically, the slidable indicator 1116 is preferably manufactured with a material that is more pliable than the material used for the unidirectional detents 1130. As a result, the slidable indicator 1116 is able to slide over the unidirectional detents 1130 while travelling along the length of the elongated member 1102.

A unidirectional detent 1130 is positioned at each incremental marking 1119. In one embodiment, each unidirectional detent 1130 permits the slidable indicator 1116 to travel along the elongated member 1102 in one direction in a more facilitated manner than in the opposite direction. In another embodiment, force must be applied to the slidable indicator 1116 in order to slide the slidable indicator 1116 along the elongated member 1102, regardless of whether the slidable indicator 1116 is moving proximally or distally. As a result, the unidirectional detents 1130 act as locking mechanisms that maintain the position of the slidable indicator 1116 along the measuring scale 1118, after a measurement of a dimension of a female reproductive organ has been taken.

Figure 12A:
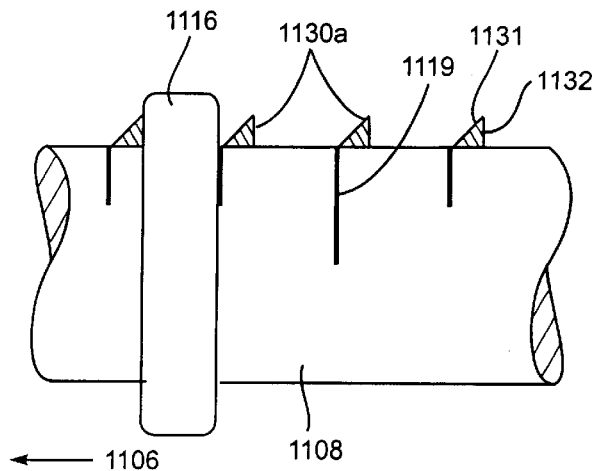
FIGS. 12a, 12b, and 12c illustrate various embodiments of the unidirectional detents.
Figure 12B:
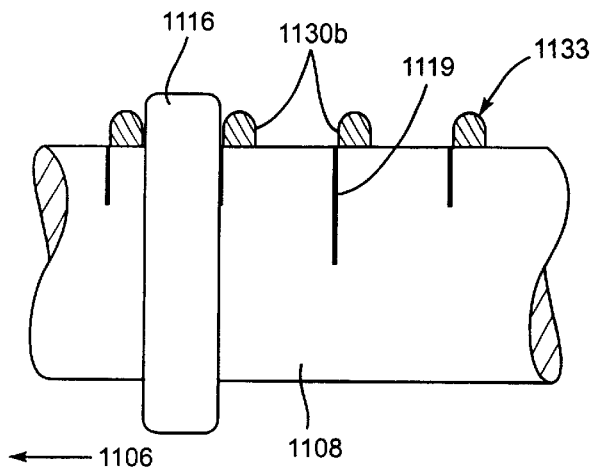
Figure 12C:
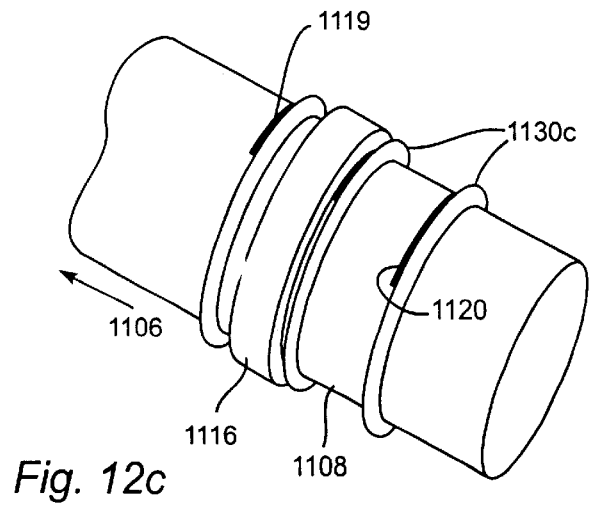

Illustrated in FIGS. 12a, 12b, and 12c are three different embodiments of unidirectional detents. Turning first to FIG. 12a, a unidirectional detent 1130a is illustrated that comprises an angled, sloping distal facing surface 1131 and a proximal face 1132 that is substantially normal, or perpendicular, to the proximal region 1108 of the elongated member 1102. The distal surface 1131 increases in slope when the universal detent 1130a is viewed in a distal to proximal direction. The slidable indicator 1116 requires less pressure to travel in a proximal direction, i.e., over the angled, sloping distal facing surface 1131, than to travel in a distal direction, i.e., against the proximal face 1132.

Turning now to FIG. 12b, a unidirectional detent 1130b is shown that is configured as a round nodule. Like the unidirectional detent 1130a in FIG. 12a, unidirectional detent 1130b also serves as a locking mechanism by preventing unwanted movement of the slidable indicator 1116 after a measurement of dimension of a female reproductive organ has been taken. With unidirectional detent 1130b, the rounded surface 1133 of the detent 1130b allows the slidable indicator 1116 to slide over the detent 1130b. Since the detent 1130b appears as an obstruction on the elongated member 1102, however, force is required to slide the slidable indicator 1116 past one of the detents 1130b in either direction. Consequently, the possibility of the slidable indicator 1116 erroneously moving from a desired position along the measuring scale 1118 is reduced since physical force must consciously be applied to the slidable indicator 1116 in order for the slidable indicator 1116 to slide past a detent 1130b in either a proximal or distal direction. FIG. 12c illustrates unidirectional detents 1130c that operate in a similar fashion as the detents 1130b in FIG. 12b. The unidirectional detents 1130c differ from the detents 1130b in that the detents 1130c extend completely around the circumference of the proximal region 1108 of the elongated member 1102, whereas the detents 1130b appear as discrete nodules.

Turning to FIG. 13, another device 1300 for measuring a dimension of a female reproductive organ that includes an elongated member 1302 adapted to be positioned within a hollow member 1304. The elongated member 1302 has a distal region 1306 and a proximal region 1308. The hollow member 1304 includes a distal opening 1310, a proximal opening 1312, and a lumen 1314. A slidable indicator 1316 is slidably engaged on the distal region 1306 of the elongated member 1302 and outside of the hollow member 1304.

Preferably, a measuring scale 1318 is located on the distal region 1306 of the elongated member 1302. The measuring scale 1318 is also preferably comprised of a plurality of incremental markings 1319 that correspond to the individual units of measure for which the device 1300 is calibrated. The measuring scale 1318 may be calibrated for any measurement system, such as, e.g., metric or English units of measure. As illustrated in FIG. 13, the incremental markings 1319 of the measuring scale 1318 are located on one side of the distal region 1306 of the elongated body 1302. In other embodiments, the markings 1319 of the measuring scale 1318 may appear on two sides of the distal region 1306, or may extend completely around the circumference of the distal region 1306. In another embodiment of the device 1300, the measuring scale 1318 will provide 1 mm incremental markings 1319 along the length of the elongated member 1302. On the device 1300, the markings 1319 start at the distal end of the elongated member 1302 and proceed proximally, such that the markings 1319 accurately reflect the length of the elongated member 1302 along any point thereof. For instance, the first marking 1319 would be one millimeter from the end of the distal end of the elongated member 1302 and would be marked with a single line indicating 1 mm.

To operate the device 1300, the elongated member 1302 is positioned within the lumen 1314 of the hollow member 1304 with the slidable indicator 1316 slidably engaged to the distal region 1306 of the elongated member 1302. Additionally, the slidable indicator 1316 is located distal from the distal opening 1310 of the hollow member 1304. Initially, the device 1300 is placed within, for example, the vagina. The device 1300 is then advanced through the vagina until the distal end of the distal region 1306 of the elongated member 1302 contacts an opposing surface in the vagina, such as, e.g., the extreme distal wall of the fornix vaginae (typically the reflection of the cervico-vagino/uterine junction either anteriorly or posteriorly). Pressure is then exerted on the hollow member 1304 in order to move the hollow member 1304 in a distal direction. As the hollow member 1304 is advanced distally, the distal opening 1310 of the hollow member 1304 will engage the slidable indicator 1316. After the hollow member 1304 engages the slidable indicator 1316, the slidable indicator 1316 will also be advanced distally with the hollow member 1304 since the slidable indicator 1316 is characterized by a diameter that is either the same as or larger than the outer diameter of the hollow member 1304. As the slidable indicator 1316 advances, the slidable indicator 1316 slides in a distal direction over the measuring scale 1318. The distal movement of the slidable indicator 1316 will stop once the slidable indicator 1316 contacts a proximal surface of the cervix. Accordingly, the position of the slidable indicator 1316 along the measuring scale 1318, after the slidable indicator 1316 contacts a proximal surface of the cervix and stops sliding distally along the distal region 1306 of the elongated member 1302, may be read in order to determine the length of the cervix. For example, the distance between the most distal incremental marking 1319 to the incremental marking 1319 located at the distal edge of the slidable indicator 1316 approximates the length of the cervix.

Illustrated in FIGS. 14a and 14b are devices 1400, 1450, respectively, for measuring a dimension of a female reproductive organ that are characterized by distal ends 1425, 1475 of increased surface area. The increased surface area of the distal ends 1425, 1475 of devices 1400, 1450 reduce the possibility of the elongated member 1402, 1452 piercing a vaginal wall by dispersing any pressure applied to a vaginal wall by the elongated member 1402, 1452. Turning to FIG. 14a, a device 1400 includes an elongated member 1402 with a distal region 1406, a proximal region 1408, and a distal end 1425. A slidable indicator 1416 is slidably engaged on the distal region 1406 of the elongated member 1402. Preferably, a measuring scale 1418 is located on the distal region 1406 of the elongated member 1402. The measuring scale 1418 is also preferably comprised of a plurality of incremental markings 1419 that correspond to the individual units of measure for which the device 1400 is calibrated. The measuring scale 1418 is calibrated and disposed along the elongated member 1402 is substantially the same manner as the measuring scale 1318 of device 1300 illustrated in FIG. 13. Accordingly, reference is made to the description of the measuring scale 1318 of device 1300 in FIG. 13 as that description also applies to the calibration and disposition of the measuring scale 1418.

The distal end 1425 of the elongated member 1402 is characterized by an increased surface area relative to, for example, the elongated member 100 of the device illustrated in FIG. 1. When the distal end 1425 contacts a vaginal wall, such as, e.g., the reflection of the cervico-vagino/uterine junction either anteriorly or posteriorly, the possibility of the elongated member 1402 puncturing the vaginal wall is reduced. Due to the increased surface area of distal end 1425, the pressure applied to the wall is dispersed along a greater surface area as compared to the elongated member 100 shown in FIG. 1. In one embodiment, the distal end 1425 is formed to substantially conform to the shape of a typical reflection of the cervico-vagino/uterine junction. Additionally, the distal end 1425 is capable of being incorporated as part of any of the elongated members of the devices disclosed herein.

The operation of device 1400 is substantially similar to the operation of the device illustrated in FIG. 1. For purposes of brevity, reference is made to the description of the operation of the device in FIG. 1 in order to describe the operation of device 1400.

Turning now to FIG. 14b, a device 1450 includes an elongated member 1452 with a distal region 1456, a proximal region 1458, and a distal end 1475. A slidable indicator 1466 is slidably engaged on the distal region 1456 of the elongated member 1452. Preferably, a measuring scale 1468 is located on the distal region 1456 of the elongated member 1452. The measuring scale 1468 is also preferably comprised of a plurality of incremental markings 1469 that correspond to the individual units of measure for which the device 1450 is calibrated. The measuring scale 1468 is calibrated and disposed along the elongated member 1452 is substantially the same manner as the measuring scale 1318 of device 1300 illustrated in FIG. 13. Accordingly, reference is made to the description of the measuring scale 1318 of device 1300 in FIG. 13 as that description also applies to the calibration and disposition of the measuring scale 1468.

The distal end 1475 of the elongated member 1452 is manufactured from a plastically deformable material, such as any appropriate elastomeric material. As a result of the deformable nature of the distal end 1475, the user of device 1450 is able to form the distal end 1475 into any desired shape, such as, e.g., a shape that conforms to the shape of a typical reflection of the cervico-vagino/uterine junction. The shape into which the distal end 1475 is formed preferably corresponds to the surface of the vagina against which the elongated member 1452 is placed during the operation of device 1450. Since the distal end 1475 is capable of being formed into a shape that conforms to a vaginal surface, any pressure exerted on the vaginal surface by the elongated member 1452 is distributed along the entire surface that contacts the distal end 1475. Therefore, the likelihood of the elongated member 1452 piercing that surface while the elongated member 1452 is manipulated within the vagina is reduced. Furthermore, the distal end 1475 is capable of being incorporated as part of any of the elongated members of any of the devices disclosed herein.

The operation of device 1450 is substantially similar to the operation of the device illustrated in FIG. 1. For purposes of brevity, reference is made to the description of the operation of the device in FIG. 1 in order to describe the operation of device 1450.

The present invention also provides various methods using the devices. For example, the invention provides a method for predicting the risk of preterm labor in an individual by the steps of: inserting into the vagina a device comprising an elongated member having a distal region and a proximal region, and a slidable indicator slidably engaged with the elongated member on the distal region, and the slidable indicator has a surface adapted to contact the cervix when the distal region of the elongated member is inserted into the vagina; until the slidable indicator contacts the cervix and the distal region contacts the cervical-uterine junction at the fornix vaginae; and determining the length of the cervix in the fornix vaginae by observing the position of the slidable indicator along said elongated member, wherein the length of the cervix in the fornix vaginae is inversely related to the risk of preterm labor.

As used herein the term "risk of preterm labor" refers to the risk that in individual will enter labor before the thirty-seventh week of gestation or pregnancy. Using the methods and devices of the present invention, this risk can be predicted either when the individual is already pregnant or when the individual is not pregnant. As such this can give the woman valuable insight on that may occur during the pregnancy. Also as used herein the term "preterm delivery" is used interchangeably with preterm birth and refers to birth of the fetus as the result of preterm labor. Accordingly, it is contemplated that preterm delivery would occur as the result of preterm labor. Because babies born prematurely may have serious health problems, practitioners try to avoid preterm labor it at all possible. If vaginal bleeding occurs or if the fetal membranes rupture, preterm labor is difficult to stop. However, if vaginal bleeding does not occur, and the membranes are not leaking amniotic fluid, bed rest with fluid given intravenously helps approximately one in two women. However, if the cervix dilates beyond 5 centimeters, labor usually continues until the baby is born. Typically, magnesium sulfate given intravenously stops labor in a majority of cases. Using the devices and methods of the present invention will indicate whether such treatment may be needed in the future.

The invention also provides a method for predicting the risk of miscarriage in an individual inserting into the vagina a device having an elongated member having a distal region and a proximal region, and a slidable indicator slidably engaged with the elongated member on the distal region, and the slidable indicator has a surface adapted to contact the cervix when the distal region of the elongated member is inserted into the vagina, until the slidable indicator contacts the cervix and the distal region contacts the cervical-uterine junction as the fornix vaginae; and determining the length of the cervix in the fornix vaginae by observing the position of the slidable indicator along the elongated member, wherein the length of the cervix in the fornix vaginae is inversely related to the risk of miscarriage.

The present invention also provides methods for predicting the ease of inducing labor by inserting into the vagina a device comprising, an elongated member having a distal region and a proximal region; and a slidable indicator slidably engaged with the elongated member on the distal region, the slidable indicator having a surface adapted to contact the cervix when the elongated member is inserted into the vagina, until the slidable indicator contacts the cervix and the distal region contacts the cervical-uterine junction at the fornix vaginae; and determining the length of the cervix in the fornix by observing the position of the slidable indicator along the elongated member, wherein the length of the cervix in the fornix vaginae is inversely related to the ease of inducing labor.

The invention further provides a method for assessing the fertility of an individual by inserting into the vagina a device having an elongated member having a distal region and a proximal region, and a slidable indicator slidably engaged with the elongated member on the distal region, and the slidable indicator has a surface adapted to contact the cervix when the distal region of the elongated member is inserted into the vagina, until the slidable indicator contacts the cervix and the distal region contacts the cervical-uterine junction at the fornix vaginae; and determining the length of the cervix in the fornix vaginae by observing the position of the slidable indicator along the elongated member, wherein the length of the cervix in the fornix vaginae is inversely related to the fertility of an individual.

As used herein, the term "fertility" refers to the ability of a female to carry a fetus to the point where it is viable or can survive with the help of medical science, if necessary, when delivered, a female attempting pregnancy, preconceptional evaluation, or procedures involved with infertility treatment. Accordingly, fertility generally refers to the ability of a female to carry a fetus to a normal nine month term, as well as to any other shorter term where the infant would survive on its own or with critical care. By assessing the cervical length and diameter, a practitioner achieves an appreciation of the fertility of the female, because a risk for preterm labor can be predicted. For example, the practitioner can determine that a female is at such a risk for preterm labor and preterm delivery that the chances of survival of the infant would be small, then the practitioner can advise the female of the risk. Accordingly, the female can make the decision to avoid pregnancy or can, with the assistance of her physician, take steps through diet, rest, and medications to lessen the risk of preterm labor.

As used herein the term "female" refers to a mammalian female, such as a human, horse, dog, cow, pig or monkey. Although the devices and methods are particularly adapted for use in a human female, one skilled in the art understands that they may be used in any female mammal. Accordingly, the devices and methods of the present invention could be used in veterinary medicine, if desired. When used in veterinary medicine, the devices and methods are specifically adapted for the type of animal on which the devices and methods will be used. For example, when used on a horse, the elongate member will be greater in length than the elongate member of a device adapted for human use. The elongate member must be of a sufficient length to enable a veterinarian to measure the length of the cervix, the dilation of the cervix, and the depth of the uterus of a female horse. Since the equine vaginal canal is longer than a human vaginal canal, the elongate member must accordingly be longer when adapted for equine use.

In addition, the invention provides methods for measuring the dilation of a cervix uteri, where the cervix uteri comprises one side and an opposite side, the method comprising, inserting into the vagina a device comprising, an elongated member having a distal region, a proximal region, and a bend in the elongated member at or near the distal region such that the distal region and the proximal region are approximately perpendicular to one another; a measuring scale on the distal region of the elongated member; and a slidable indicator slidably engaged with the elongated member on the distal region, the slidable indicator having a surface adapted to contact one side of the cervix uteri when the distal region of the elongated member is inserted into the vagina, until the slidable indicator contacts one side of the cervix uteri at or near the external os; moving the device laterally such that the slidable indicator remains in contact with one side of the cervix uteri at or near the external os and such that the slidable indicator slides along the elongated member until an end of the elongated member at the distal region is in alignment with the opposite side of the cervix uteri at or near the external os; and determining the dilation of the cervix uteri by observing the position of the slidable indicator on the measuring scale on the elongated member.

The invention further provides for a method of determining a dimension of a female reproductive by using any of the aforementioned devices of the present invention to measure the dimension without visually observing the device as the measurement is being performed. The device suitable for use with this method will include at least an elongated member having a distal region, a proximal region, and a measuring scale disposed on the elongated member, and a slidable indicator slidably engaged to the elongated member and positionable along the measuring scale. Preferably, the measuring scale is disposed on the distal region of the elongated member. Additionally, the measuring scale comprises a plurality of incremental markings. Initially, the slidable indicator is preferably positioned proximally from the most proximal incremental marking of the measuring scale. A user first grasps the slidable indicator manually, with, for example, an index finger and a third finger. The user then inserts the device into the vagina by manipulating the device into the vagina, using the slidable indicator to position the device. The device is advanced within the vagina distally until the distal end of the distal region of the elongated member comes into contact with an extreme distal wall of the fornix vaginae, such as, e.g., the reflection of the cervico-vagino/uterine junction either anteriorly or posteriorly. The slidable indicator is then progressed distally along the elongated member until contact is made between the slidable indicator and the reproductive organ being measured. The length of the reproductive organ is determined by observing the position of the slidable indicator along the measuring scale. The position of the slidable indicator along the measuring scale is approximately the length of the reproductive organ.

The invention also provides for a method for determining a dimension of a female reproductive organ through the use of a device comprising an elongated member having a distal region and a proximal region, wherein the elongated member has a measuring scale on the distal region. In one embodiment of this method, the device used in the method does not have a slidable indicator that is slidably engaged with the elongated member, unlike the other devices provided for by this invention. This method is useful when the cervix of a patient is clearly visible from outside of the patient's body. For example, a speculum is first inserted into the vaginal orifice in order to facilitate a clear view of the vaginal walls and the cervix. With the speculum in place, the distal region of the elongated member is inserted into the vagina. The elongated member is advanced within the vagina towards the cervix. The elongated member is then oriented adjacent to the cervix such that the measuring scale on the distal region is visible to the person measuring the cervix. Next, the elongated member is advanced until the distal region contacts the cervical-uterine junction at the fornix vaginae. The length of the cervix is then determined by comparing the cervix with the measuring scale on the distal region of the elongated member. A light source may additionally be used to direct light into the vaginal orifice towards the cervix, thereby increasing the clarity with which the cervix and the measuring scale are observed from outside of the patient's body.

EXAMPLE 1

Cervix Length Measurement

This example provides measurement of the length of the cervix in the vagina in a subject and correlation with reported criteria for determining the risk of preterm delivery.

The subject preferably lies in a prone position on her back. The practitioner uses a speculum to first examine the vaginal cavity and to observe the optimum position for placing the device. The practitioner inserts into the vagina a device comprising an elongated member having a distal region and a proximal region and a slidable indicator slidably engaged with the elongated member on the distal region, said slidable indicator having a surface adapted to contact the cervix when the distal region of the elongated member is inserted into the vagina. The device is inserted until the slidable indicator contacts the cervix and the distal region contacts the cervical-uterine junction at the fornix vaginae. Then the length of the cervix in the fornix vaginae is determined by observing the position of the slidable indicator on the elongated member. Since length of the cervix in the fornix vaginae is inversely related to the risk of preterm delivery, such a risk can be determined. The practitioner uses the data provided herein in Table 1, which is discussed in Iams et al., *N. Eng. J. Med.* 334:567 (1996); which is also incorporated by reference herein, in order to determine the relative risk of preterm delivery.

TABLE I

| | Relative Risk of Preterm Delivery | | |
|---|---|---|---|
| Length of cervix (mm) | Percentile | at 24 weeks | at 28 weeks |
| 40 | ≦75 | 2 | 2.8 |
| 35 | ≦50 | 2.4 | 3.5 |
| 30 | ≦25 | 3.8 | 5.4 |
| 26 | ≦10 | 6.2 | 9.6 |
| 22 | ≦5 | 9.5 | 13.9 |
| 13 | ≦1 | 14 | 24.9 |

As used herein, the term "relative risk" refers to the likelihood that there will be a preterm delivery when compared to the population which does not have that finding. In this subject, the length of the cervix is determined to be 22 mm. Since the subject is at 24 weeks of gestation, the relative risk for preterm delivery for this subject is 9.5. In other words, this subject has a 9.5 higher risk for preterm delivery than an individual whose cervix is greater than 22 mm in length.

EXAMPLE II

Cervix Dilation Measurement

This example demonstrates the use of the invention disclosed herein to measure the dilation of the cervix uteri in the same subject as in Example 1, to predict the risk for preterm delivery or the particular stage of delivery in a normal pregnancy.

Using a device of the present invention to measure the dilation of the cervix uteri, the practitioner inserts into the vagina a device comprising, an elongated member having a distal region, a proximal region, and a bend in the elongated member at or near the distal region such that the distal region and the proximal region are approximately perpendicular to one another; a measuring scale on the distal region of the elongated member; and a slidable indicator slidably engaged with the elongated member on the distal region, the slidable indicator having a surface adapted to contact one side of the cervix uteri when the distal region of the elongated member is inserted into the vagina, until the slidable indicator contacts one side of the cervix uteri at or near the external os. The practitioner then moves the device laterally such that the slidable indicator remains in contact with one side of the cervix uteri at or near the external os and such that the slidable indicator slides along the elongated member until an end of the elongated member at the distal region is in alignment with the opposite side of the cervix uteri at or near the external os. The practitioner determines the dilation of the cervix uteri by observing the position of the slidable indicator on the measuring scale on the elongated member. Using this procedure, the dilation of the cervix uteri is this subject is found to be 5 cm. Accordingly, the physician advises the subject that delivery is imminent. Since this subject is in her $24^{th}$ week of pregnancy, this delivery is premature or preterm.

Although the invention has been described with reference to the examples provided above, it should be understood that various modifications can be made without departing from the spirit of the invention. Accordingly, the invention is limited only by the claims.

What is claimed is:

1. A device for determining a dimension of a female reproductive organ comprising:

a hollow member having a distal opening, a proximal opening, and a lumen, wherein the distal opening of the hollow member is adapted to contact the reproductive organ;

an elongated member positioned within the lumen of the hollow member, the elongated member having a distal region and a proximal region; and a slidable indicator slidably engaged with the elongated member on the proximal region of the elongated member.

2. The device of claim 1 further comprising a measuring scale disposed on the proximal region of the elongated member.

3. The device of claim 2 further comprising a hand grip disposed on the proximal region of the elongated member and located proximal from the measuring scale, wherein the hand grip has a diameter greater than a diameter of the elongated member, thereby preventing the slidable indicator from sliding beyond the measuring scale in a proximal direction.

4. The device of claim 1 further comprising:

a first measuring scale disposed on the proximal region of the elongated member; and a second measuring scale disposed on the distal region of the elongated member.

5. The device of claim 4 further comprising:

a second slidable indicator slidably engaged on the distal region of the elongated member.

6. The device of claim 1 wherein the hollow member further comprises an observation opening located towards the distal opening of the hollow member to allow visual confirmation of the elongated member as the elongated member travels within the lumen of the hollow member.

7. The device of claim 2 wherein the hollow member further comprises an observation opening located towards the proximal opening of the hollow member to allow visual confirmation of the elongated member as the elongated member travels within the lumen of the hollow member and to enable visual confirmation of the measuring scale while the elongated member is disposed within the lumen.

8. The device of claim 1 wherein the distal opening of the hollow member is adapted to contact the reproductive organ while simultaneously allowing the elongated member to travel through the distal opening and distally beyond the reproductive organ.

9. The device of claim 6 wherein the reproductive organ is a cervix, the dimension is the length of the cervix, and the elongated member travels distally beyond the cervix into the fornix vaginae.

10. The device of claim 1 wherein the proximal opening of the hollow member is adapted to engage the slidable indicator and prevent the slidable indicator from sliding distally along the elongated member.

11. A device for determining a dimension of a female reproductive organ comprising:

a hollow member having a distal opening, a proximal opening, and a lumen;

an elongated member capable of being disposed within the lumen of the hollow member, the elongated member having a distal region, a proximal region, and a measuring scale located on the proximal region; and a slidable indicator slidably engaged on the proximal region of the elongated member.

12. The device of claim 11 further comprising a plurality of unidirectional detents located on the proximal region of the elongated member.

13. The device of claim 11 wherein the measuring scale is comprised of incremental markings, and the device further comprises:

a unidirectional detent located at each marking of the measuring scale.

14. The device of claim 13 further comprising a hand grip in operable connection with the proximal region of the elongated member and positioned proximal from the measuring scale.

15. The device of claim 11 further comprising a second measuring scale located on the distal region of the elongated member.

16. The device of claim 15 further comprising a second slidable indicator slidably disposed on the distal region of the elongated member.

17. The device of claim 11 wherein the reproductive organ is a cervix, the dimension is the length of the cervix, and the elongated member is capable of being progressed distally within the lumen of the hollow member, past the distal opening of the hollow member, and distally beyond the cervix into the fornix vaginae.

18. The device of claim 17 wherein the hollow member has a diameter sufficiently wide to enable the hollow member to maintain simultaneous contact with a wall of the fornix vaginae and a proximal end of the cervix.

19. The device of claim 18 wherein the elongated member has a diameter narrower than the diameter of the hollow member, and wherein the diameter of the elongated member is sufficiently narrow to enable the elongated member to be inserted into the lumen of the hollow member, progressed through the hollow member and distally beyond the cervix into the fornix vaginae.

20. A device for determining the length of a cervix comprising:

a hollow member having a distal opening, a proximal opening, and a lumen, wherein the distal opening is adapted to contact the proximal surface of the cervix;

an elongated member positionable within the lumen of the hollow member, the elongated member having a distal region, a proximal region, and a measuring scale incorporated on the proximal region; and a slidable indicator slidably engaged on the proximal region of the elongated member;

wherein the hollow member has a diameter sufficiently wide to permit the distal opening of the hollow member to maintain in simultaneous contact with a wall of a fornix vaginae and the proximal surface of the cervix and wherein the elongated member has a diameter narrower than the diameter of the hollow member and sufficiently narrow to enable the elongated member to be progressed through the lumen of the hollow member and distally outside of the distal opening of the hollow member, beyond the proximal surface of the cervix, and into the fornix vaginae.

21. The device of claim 20 wherein the measuring scale is comprised of incremental markings, and the device further comprises:

a plurality of unidirectional detents disposed on the proximal region of the elongated member, wherein a unidirectional detent is positioned at each incremental marking of the measuring scale.

22. The device of claim 21 wherein the slidable indicator comprises a first material and the universal detents comprise a second material, the first material being more pliable than the second material, thereby enabling the slidable indicator to slide over the unidirectional detents.

23. The device of claim 20 further comprising an observation opening located on the hollow member towards the distal opening of the hollow member to facilitate visual observation of the elongated member while the elongated member is progressed within the lumen of the hollow member.

24. The device of claim 20 further comprising an observation opening located on the hollow member towards the proximal opening of the hollow member to facilitate visual observation of the elongated member while the elongated member is progressed within the lumen of the hollow member and to facilitate visual observation of the measuring scale while the elongated member is disposed within the lumen of the hollow member.

25. A method of measuring a length of a cervix within a vagina, comprising:

inserting an elongated member into a proximal opening of a hollow member and into a lumen of the hollow member, the elongated member having a distal region, a proximal region, and a slidable indicator slidably engaged to the proximal region, and the hollow member further comprises a distal opening;

inserting the hollow member, with the elongated member disposed therein, into the vagina;

advancing the hollow member within the vagina until the distal opening of the hollow member is in operable contact with a proximal end of the cervix;

advancing the elongated member distally through the lumen of the hollow member until the distal region of the elongated member is in operable contact with a cervical-uterine junction; and determining the length of the cervix by observing the position of the slidable indicator along the proximal region of the elongated member.

26. The method of claim 25 wherein the elongated member further comprises a measuring scale disposed on the proximal region of the elongated member, and the determining the length of the cervix step is performed by observing the position of the slidable indicator relative to the measuring scale.

27. The method of claim 26 wherein the measuring scale comprises a plurality of incremental markings oriented such that the most distal marking is positioned at the proximal opening of the hollow member when the distal region of the elongated member is positioned at the distal opening of the hollow member and, prior to the advancing the elongated member step, further comprising:

positioning the slidable indicator at the distal opening of the hollow member.

* * * * *